United States Patent
Azab et al.

(10) Patent No.: US 12,220,465 B2
(45) Date of Patent: Feb. 11, 2025

(54) COMPOSITIONS AND METHODS FOR TARGETED TREATMENT AND IMAGING OF CANCER OR TUMORS

(71) Applicant: Washington University, St. Louis, MO (US)

(72) Inventors: Abdel Kareem Azab, St. Louis, MO (US); Barbara Muz, St. Louis, MO (US)

(73) Assignee: Washington University, St. Louis, MO (US)

( * ) Notice: Subject to any disclaimer, the term of this patent is extended or adjusted under 35 U.S.C. 154(b) by 1065 days.

(21) Appl. No.: 16/698,068

(22) Filed: Nov. 27, 2019

(65) Prior Publication Data
US 2020/0179520 A1 Jun. 11, 2020

Related U.S. Application Data

(60) Provisional application No. 62/772,365, filed on Nov. 28, 2018.

(51) Int. Cl.
| | |
|---|---|
| *A61K 47/46* | (2006.01) |
| *A61K 51/04* | (2006.01) |
| *A61K 51/12* | (2006.01) |
| *C12N 5/071* | (2010.01) |
| *A61K 45/06* | (2006.01) |
| *A61K 49/00* | (2006.01) |

(52) U.S. Cl.
CPC ...... *A61K 51/0491* (2013.01); *A61K 51/1244* (2013.01); *C12N 5/0692* (2013.01); *A61K 45/06* (2013.01); *A61K 49/0017* (2013.01); *C12N 2500/02* (2013.01); *C12N 2502/30* (2013.01)

(58) Field of Classification Search
CPC .................................................. C12N 5/0692
See application file for complete search history.

(56) References Cited

U.S. PATENT DOCUMENTS

| | | | |
|---|---|---|---|
| 8,491,887 B2 | 7/2013 | Mizukami et al. | |
| 9,857,360 B2* | 1/2018 | Lim | G01N 33/5091 |
| 2006/0051330 A1* | 3/2006 | Hossfeld | C12N 5/0607 |
| | | | 435/368 |
| 2007/0264231 A1 | 11/2007 | Gianni et al. | |
| 2009/0124007 A1 | 5/2009 | Cho | |
| 2012/0295347 A1* | 11/2012 | Kessler | C12N 5/0692 |
| | | | 435/325 |
| 2017/0015685 A1* | 1/2017 | Sato | C12Q 1/16 |

OTHER PUBLICATIONS

Defresne et al. "Preconditioned Endothelial Progenitor Cells Reduce Formation of Melanoma Metastases through SPARC-Driven Cell-Cell Interactions and Endocytosis" Cancer Res; 71(14) Jul. 15, 2011, 10 pages (Year: 2011).*
Teng et al. "Conditioned media from human ovarian cancer endothelial progenitor cells induces ovarian cancer cell migration by activating epithelial-to-mesenchymal transition" Cancer Gene Therapy (2015) 22, 518-523 (Year: 2015).*
Wang et al. "Endothelial progenitor cell-conditioned medium promotes angiogenesis and is neuroprotective after spinal cord injury" Neural Regeneration Research 13(5):887-895, 2018 (Year: 2018).*
Anna Laurenzana et al. "Endothelial Progenitor Cells as Shuttle of Anticancer Agents" Human Gene Therapy, vol. 27 No. 10, 784-791., 2016 (Year: 2016).*
Aicher, A. et al., "Mobilizing Endothelial Progenitor Cells," Hypertension, Mar. 1, 2005, pp. 321-325, vol. 45, No. 3.
Asahara, T. et al., "Isolation of Putative Progenitor Endothelial Cells for Angiogenesis," Sci., Feb. 14, 1997, pp. 964-967, vol. 275.
Calzi, S. et al., "EPCs and Pathological Angiogenesis: When Good Cells Go Bad," NIH Public Access Author Manuscript, May 10, 2013, pp. 1-18, published in final edited form as: Microvasc. Res., May 2010, pp. 207-216, vol. 79, No. 3.
Chung, Y. et al., "Human Embryonic Stem Cell Lines Generated without Embryo Destruction," Cell Stem Cell, Feb. 2008, pp. 113-117, vol. 2.
De La Puente, P. et al., "Cell Trafficking of Endothelial Progenitor Cells in Tumor Progression," Clin. Cancer Res., 2013, pp. 3360-3368, vol. 19, No. 13.
Elhai, J. et al., "Conjugal Transfer of DNA to Cyanobacteria," Methods in Enzymology, 1988, pp. 747-754, vol. 167.
Klimanskaya, I. et al., "Human embryonic stem cell lines derived from single blastomeres," Nature, Nov. 23, 2006, pp. 481-485, vol. 444, with Addendum, p. 512, and Corrigendum, Nat., Mar. 15, 2007, p. 342, vol. 446.
Laurenzana, A. et al., "Melanoma cell therapy: Endothelial progenitor cells as shuttle of the MMP12 uPAR- degrading enzyme," Oncotarget, 2014, pp. 3711-3727, vol. 5, No. 11.
Liu, J. et al., "The origins of vacularization in tumors," Frontiers Biosci., Jun. 1, 2012, pp. 2559-2565, vol. 17.
Peichev, M. et al., "Expression of VEGFR-2 and AC133 by circulating human CD34+ cells identifies a population of functional endothelial precursors," Blood, Feb. 1, 2000, pp. 952-958, vol. 95, No. 3.
Purwanti, Y. et al., "Antitumor Effects of CD40 Ligand-Expressing Endothelial Progenitor Cells Derived From Human Induced Pluripotent Stems Cells in a Metastatic Breast Cancer Model," Stem Cells Translational Med., 2014, pp. 923-935, vol. 3.
Reyes, M. et al., "Origin of endothelial progenitors in human postnatal bone marrow," J. Clin. Invest., 2002, pp. 337-346, vol. 109, No. 3.
Shi, Q. et al., "Evidence for Circulating Bone Marrow-Derived Endothelial Cells," Blood, Jul. 15, 1998, pp. 362-367, vol. 92, No. 2.

(Continued)

*Primary Examiner* — Thane Underdahl
(74) *Attorney, Agent, or Firm* — Polsinelli PC

(57) ABSTRACT

Among the various aspects of the present disclosure is the provision of compositions and methods for targeted treatment and imaging of cancers or tumors.

7 Claims, 21 Drawing Sheets
(15 of 21 Drawing Sheet(s) Filed in Color)

(56) References Cited

OTHER PUBLICATIONS

Studier, W., "Protein production by auto-induction in high-density cultures," Protein Expr. Purif., 2005, pp. 207-234, vol. 41.

Takahashi, K. et al., "Induction of Pluripotent Stem Cells from Adult Human Fibroblasts by Defined Factors," Cell, Nov. 30, 2007, pp. 861-872, vol. 131.

Urbich, C. et al., "Endothelial Progenitor Cells. Characterization and Role in Vascular Biology," Circ. Res., 2004, pp. 343-353, vol. 95.

Zhou, H. et al., "Generation of Induced Pluripotent Stem Cells Using Recombinant Proteins," Cell Stem Cell, May 8, 2009, pp. 381-384, vol. 4.

* cited by examiner

| Ratio of EPC : Tumor | Boron Content ng/mg Tissue |
|---|---|
| 0.01:1 | 17.2 |
| 0.05:1 | 82.7 |
| 0.1:1 | 158.0 |
| 0.25:1 | 347.5 |
| 0.5:1 | 579.2 |
| 1:1 | 868.8 |

Amount needed for successful BNCT is ~20 ng $^{10}$B/mg tissue

Pre-inj.     30min     24h

COMPOSITIONS AND METHODS FOR TARGETED TREATMENT AND IMAGING OF CANCER OR TUMORS

CROSS REFERENCE TO RELATED APPLICATIONS

This application claims the benefit of U.S. Provisional Application No. 62/772,365, filed Nov. 28, 2018, the disclosure of which is hereby incorporated by reference in its entirety.

FIELD OF THE TECHNOLOGY

The present disclosure generally relates to methods and compositions for treating and imaging cancer.

BACKGROUND

Examples of conventional methods for tumor (cancer) treatment include treatment methods using chemical anti-cancer agents or radiation. However, the main limiting factor of cancer treatment is the side effects to normal tissues induced by the therapy. These limitations apply to radiotherapy, chemotherapy, biological agents and nano-particulate drug delivery systems, due to lack of specificity. Immunotherapy (such as CAR T cells) has emerged as a promising approach to treat cancer, in which immune cells are isolated from the patient, genetically engineered to express receptors that target the tumor and injected back to the patient for treatment. However, these cells lack the ability to specifically home to the tumor, and tumor-type dependent efficacy, since it depends on specific antigen expression, which limits its use to one type of cancer and even to certain clonal subsets of the same tumor since tumors can be a heterogeneous mix of different clones that may express different antigens.

Therefore, an immunotherapy with preferential tumor targeting, with a broader application among different cancers is dearly needed.

SUMMARY

The present disclosure is based on the provision of compositions and methods for targeted treatment and imaging of cancers or tumors.

Accordingly, one aspect of the present disclosure features a delivery system comprising a population of endothelial progenitor cells (EPCs) labeled with an imaging agent or a therapeutic agent. In some examples, the population of EPCs is obtained from bone marrow, peripheral blood, cord blood, or fat tissue. In other examples, the population of EPCs is generated from a pluripotent stem cell or an induced pluripotent stem cell.

In some examples, the compositions include EPCs labeled with an imaging agent where the imaging agent is one or more of a fluorophore, nanoparticle, radioisotope, radionuclide, bioluminescence imaging agent, MRI contrast agent, and X-ray/CT contrast agent. In some examples, the imaging agent is one or more of 18F-Fluorodeoxyglucose, Zirconium-89 and LS-542 dye.

In some instances, the compositions include EPCs labeled with a therapeutic agent where the therapeutic agent is one or more of an anti-neoplastic agent, photodynamic therapy pro-drug, boron-containing compound, mitotic inhibitor, immune-related agent, biological response modifier, vitamin, peptide, anti-inflammatory, and radioactive particles.

In some examples, the population of EPCs is cultured with a priming medium, wherein the priming medium is a cancer cell condition medium or a hypoxic cancer cell conditioned medium.

In one aspect of the disclosure provides a method of detecting a tumor or a cancer cell in a subject having or suspected of having a tumor or cancer. In some instances the methods comprise administering a delivery system comprising a population of EPCs labeled with an imaging agent to the subject and measuring a signal from the imaging agent. In some examples. The methods comprise obtaining a population of endothelial progenitor cells (EPCs); and contacting the EPCs with an imaging agent under conditions sufficient for labeling the EPCs with the imaging agent. In a specific example, the population of EPCs is obtained from the subject.

In some aspects the methods include classifying the subject as having or not having cancer, wherein the subject is classified as having cancer if the signal of the imaging agent is increased relative to a control or the subject is classified as not having cancer if the signal of the reporter molecule is the same or decreased relative to a control.

In some embodiments, the methods include EPCs labeled with an imaging agent where the imaging agent is one or more of a fluorophore, nanoparticle, radioisotope, radionuclide, bioluminescence imaging agent, MRI contrast agent, and X-ray/CT contrast agent.

In some examples, the methods include contacting the population of EPCs with a priming medium, wherein the priming medium is a cancer cell condition medium or a hypoxic cancer cell conditioned medium.

In some examples, the delivery system does not substantially accumulate in non-malignant tissues.

In another aspect, the present disclosure provides a method of killing a tumor or a cancer cell in a subject in need thereof. In some instances the methods comprise administering a delivery system comprising a population of EPCs labeled with a therapeutic agent to the subject. In some examples, the methods include obtaining a population of EPCs from the subject; and contacting the EPCs with a therapeutic agent under conditions sufficient for labeling the EPCs with the therapeutic agent. In a specific example the population of EPCs is obtained from the subject.

In some examples, the methods include EPCs labeled with a therapeutic agent where the therapeutic agent is one or more of a is one or more of an anti-neoplastic agent, photodynamic therapy pro-drug, boron-containing compound, mitotic inhibitor, immune-related agent, biological response modifier, vitamin, peptide, anti-inflammatory, and radioactive particle.

In some examples, the methods include contacting the population of EPCs with a priming medium, wherein the priming medium is a cancer cell condition medium or a hypoxic cancer cell conditioned medium.

Other features or advantages of the present invention will be apparent from the following drawings and detailed description of several examples, and also from the appended claims.

BRIEF DESCRIPTION OF THE FIGURES

The application file contains at least one drawing executed in color. Copies of this patent application publication with color drawing(s) will be provided by the Office upon request and payment of the necessary fee.

FIG. 1A: are graphs showing expression of EPC markers on EPCs isolated from cord blood. FIG. 1B: are graphs showing expression of EPC markers on EPCs isolated from bone marrow (BM). FIG. 1C: are graphs showing expression of EPC markers on EPCs isolated from fat tissue.

FIG. 3A: is a bar graph showing the migration of EPCs to hematologic tumors such as multiple myeloma—MM.1S in a tumor-size-dependent manner. FIG. 3B: is a bar graph showing the migration of EPCs to solid tumors such as lung cancer—A549 in a tumor-size-dependent manner.

FIG. 5A: graphically depicts EPCs homing to BxPC3 pancreatic cancer cell line injected under the skin of nude mice. FIG. 5B: graphically depicts EPCs homing to an orthotopic glioma model by injecting GL261 glioma cells intracranially into the C57BL/6J mice. FIG. 5C: graphically depicts EPCs homing to a metastatic lung cancer model by injecting Lewis lung cancer (LLC) cells intravenously (IV) to C57BL/6J mice which results in developing lung nodules as well as liver metastasis. FIG. 5D: graphically depicts EPCs homing to an orthotopic localized breast cancer model by implanting B01-GFP+ breast cancer cells into the mammary fat pad of C57BL/6J mice, which shows restricted tumor growth in the mammary fat pad within the first 3 days post-implantation. FIG. 5E: graphically depicts EPCs homing to a metastatic breast cancer model detected as B01-GFP+ cell in multiple distant organs.

FIG. 6A: is a bar graph depicting EPCs prevalence using flow cytometry showing the disease was small; while at two weeks post injection the disease was advanced. FIG. 6B: is a bar graph and image showing a disseminated MM model by injection of MM.1S-GFP-Luc+ cells IV, and after 4 weeks we confirmed tumor development by bioluminescence imaging (BLI), which found to be mainly in the BM in the femur, with low signal in the liver and spleen. FIG. 6C: is a graph showing the correlation between tumor size and migration of EPCs in vitro.

FIG. 7A: is a bar graph showing EPCs with MM-conditioned media improved the migration of EPCs (2-fold of non-conditioned) and the priming with hypoxic MM media improved the migration in vitro modestly. FIG. 7B: is a bar graph showing in vivo, the effect was more significant; "priming" with conditioned media from normoxic MM cells improved the homing of EPCs about 7-fold, while media from hypoxic MM cells about 27-fold compared to non-primed EPCs.

FIG. 8A: is a bar graph showing BTZ kills myeloma cells at low concentration (IC50 of 5 nM). FIG. 8B: is a bar graph showing EPCs are not sensitive to BTZ up to 50 nM. FIG. 8C: is a bar graph showing migration of BTZ loaded EPCs towards cancer cells. FIG. 8D: is a bar graph showing BTZ-loaded-EPCs killed MM cells in a dose-dependent manner.

FIG. 9A: is a bar graph showing titanocene as a prodrug loaded it to EPCs had no effect on the survival of EPCs. FIG. 9B: is a bar graph showing the presence of Titanium in the EPCs using inductively coupled plasma mass spectrometry (ICP-MS). FIG. 9C: is a bar graph showing titanocene loaded EPCs migrate towards cancer cells. FIG. 9D: is a bar graph showing EPCs loaded with titanocene and then activated using the position emission caused killing of MM cells in a dose-dependent manner.

FIG. 10A: is a bar graph showing BPA had no effect on the survival of EPCs. FIG. 10B: is a bar graph showing 4-borono-L-phenylalanine loaded EPCs migrate towards cancer cells. FIG. 10C: is a bar graph showing that EPCs where actually loaded with boron by detecting its presence in the EPCs using inductively coupled plasma mass spectrometry (ICP-MS). FIG. 10D: is a table showing that any ration above 2.5% of loaded EPCs was enough to meet the threshold for successful BNCT, in the higher cases of 1:1 ratio, the amount of boron detected was about 40-fold higher than the amount needed for BNCT.

FIG. 11A: is a bar graph showing the dye does not cause any cytotoxic effects in EPCs. FIG. 11B: is a bar graph showing LS-542 labeled EPCs migrate towards cancer cells. FIG. 11C: is a bar graph showing the labeling efficiency of EPCs with LS-542 was directly proportional with the concentration based on relative mean fluorescent intensity (RMFI) detected by flow cytometry. FIG. 11D: include IR images showing labeled EPCs accumulated in the breast cancer tumor specifically, which can be detected using an NIR imaging camera.

FIG. 12A: is a bar graph showing EPCs were efficiently radiolabeled with $^{18}$F-FDG. FIG. 12B: is a bar graphs showing EPCs were efficiently radiolabeled with $^{89}$Zr-oxine. FIG. 12C: is a bar graph showing EPCs were efficiently radiolabeled with $^{64}$Gd.

DETAILED DESCRIPTION

Figure 1A:
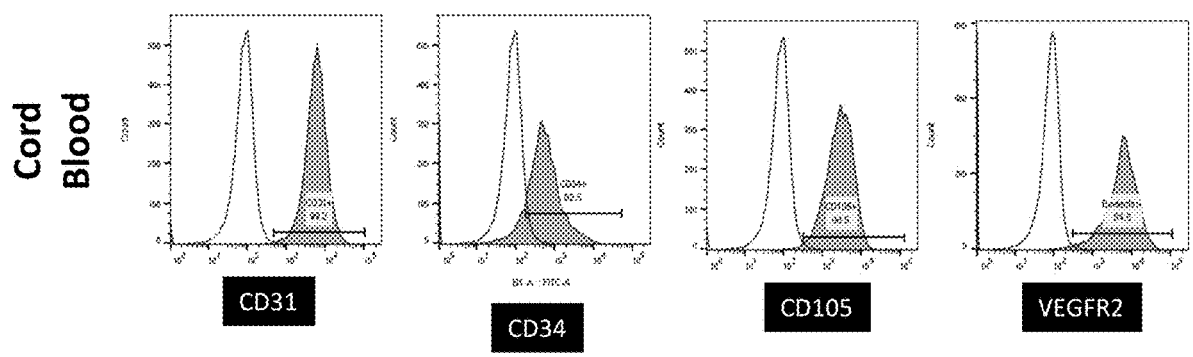
FIG. 1A-C show graphs of EPC surface markers on EPCs isolated from different tissues.

Cancer is responsible for 25% deaths in the USA, with estimated 1,685,210 new cases and 595,690 people will die from the disease each year. An estimated 14.1 million new cases and 8.2 million deaths from the disease each year worldwide. Despite the fact that the success rate for chemotherapy has risen every year for the past decades, extending the life of patients by reducing the risk of cancer recurrence, it is related to multiple adverse effects. Chemotherapy is a systemic therapy working through the whole body, which kills cancer cells but also healthy cells in the bone marrow, digestive tract, and hair follicles, which may cause life-threatening infections due to leukopenia, loss of appetite and alopecia (hair loss). The emphasis in cancer treatment in general has shifted from cytotoxic, non-specific chemotherapies to molecularly targeted, rationally designed therapies promising greater efficacy.

Most targeted therapies specific for cancer cells are either small molecules (targeting mainly intracellular components), monoclonal antibodies (targeting cell surface molecules), or nanoparticles (NPs). NPs and nanoscale technologies are changing the scientific landscape in terms of cancer detection, treatment, and prevention. The small size, improved solubility, and customized surface by "decorating" NPs thus superior cancer targeting, and multi-functionality by "loading" NPs with therapy provides number of biomedical applications. However, synthetic drug delivery systems have considerable pharmacokinetic and pharmacodynamic disadvantages, such as accumulation in the liver and other filtrating organs. A better strategy to specifically target any cancer cells and improve drug delivery for better treatment efficacy, while reducing side effects in normal tissues are urgently needed.

Endothelial progenitor cells (EPCs) are involved in the development of angiogenesis (generation of new blood vessels) in all cancer types. The EPCs mobilize from the bone marrow in response to "hypoxic" signals from cancer cells in the tumor site, through secretion of cytokines from the tumor cells to the blood; the EPCs are activated by these cytokines and extravasate to the blood. EPCs then home specifically to the tumor through chemotaxis (according to cytokines concentration gradient), and find their way to the highest concentration of cytokines, which is found in the tumor, not in normal organs. The use of EPCs as a delivery vehicle for therapy can circumvent the limitations of classic cellular immunotherapy. (1) the EPCs have the capability of cell-trafficking and specific homing to the tumors and not to other normal tissues. In addition, this highly specific and efficient biological machinery targeting tumors, can be further enhanced with "priming" EPCs using cancer-derived media and/or hypoxic tumor media. An advantage of using EPCs is that it does not need viral (or non-viral) gene editing of the cells; the only requirement is EPCs mobilization, harvest, and 'labeling' EPCs by a few-hour ex vivo incubation with the imaging or therapeutic agent. Unlike immunosuppression in advanced tumor stages, the more advanced the tumor the higher number of EPCs are present in the circulation of the patient, therefore this therapy will also work in immunosuppressed patients.

Moreover, EPCs do not activate the immune system, and their toxicity is limited to the therapeutic agent they are labeled with. In some aspects, EPCs circumvent the toxicity of a therapeutic agent through labeling with "inducible" therapies (see, e.g., Cerenkov radiation below), thereby controlling the level of EPCs toxicity in vivo. Finally, unlike engineered/targeted immunotherapies such as cellular (CAR-T cells), bispecific T cell engagers, or monoclonal antibodies that target specific molecules on a specific tumor type, EPCs can be used as a pan-cancer "Trojan-horse" drug-delivery system due to the universality of (angiogenesis) in all cancer types.

The present disclosure is based, at least in part, in the development of a delivery system which has the ability to overcome the limitations of the synthetic drug delivery systems as well as immunotherapies. This system utilizes the patho-physiologic mechanism of specific homing of EPCs to cancer to achieve specific therapy and imaging of cancer. Accordingly, the delivery system as disclosed herein provides a new class of cellular-therapy that specifically targets tumors and avoids normal tissues. In some embodiments, the disclosed delivery system is used for used for therapeutic and/or diagnostic approaches in cancer. As demonstrated below in the specific examples, the disclosed delivery system shows pan-cancer homing capability and allows for efficient detection or treatment of cancers cells. Therefore, the present disclosure provides a delivery system, which can: (1) specifically and effectively deliver therapeutic agent to cancer cells and solid tumors; (2) improve therapeutic efficacy and reduce adverse side effects of therapeutic agents; and (3) increase detection of cancer. Compositions and methods of the delivery system are described below.

I. Delivery System

Aspects described herein stem, at least in part, from development of a delivery system comprising a population of endothelial progenitor cells. One aspect of the present disclosure encompasses EPCs which are labeled with an imaging agent and/or therapeutic agent.

As used herein, the term "progenitor cell" refers to a cell committed to differentiate into a specific type of cell or to form a specific type of tissue, and the term "endothelial progenitor cell" means a cell which can secrete an angiogenic growth factor to contribute indirectly to blood vessel regeneration or can differentiate directly into a mature endothelial cell. EPCs are a subtype of stem cells with high proliferative potential located mainly in the bone marrow and in the context of cancer, home specifically to and play a role in the neo-angiogenesis in all types of tumors. EPCs are distinguished at different stages of differentiation through CD marker expression; the bone marrow EPCs express stem cell markers CD133 and CD34; blood circulating EPCs express more mature markers including CD31, CD146, CD144; whereas terminally differentiated endothelial cells are characterized by VEGFR-2, CD31, CD146, VE-cadherin, eNOS, and vWF. In some embodiments, the EPCs suitable for use in the delivery system are CD31+, CD34+, CD105+, and/or VEGFR2+. In one aspect, the EPCs suitable for use in the present disclosure are CD34+ and CD31+. In another aspect, the EPCs are CD133+, CD34+ and VEGFR-2+. In still another aspect, the EPCs are CD133+/−, CD34+, VEGFR-2+, CD31+ and CD146+.

EPCs may be obtained from any suitable source of EPCs known in the art including, but not limited to, EPCs collected from a subject. The subject may be a subject having or suspected of having a cancer or tumor or a subject of the same species as the subject having or suspected of having a cancer or tumor. The collected EPCs may be expanded ex vivo using methods commonly known in the art.

In some embodiments, the EPCs may be obtained from a number of sources. Non-limiting examples include, from bone marrow, peripheral blood or cord blood, and fat tissue. Methods of isolating EPCs from various sources are known in the art, including methods as disclosed in Science, 275 (5302): 964-7 (1997); Blood, 95(3): 952-8 (2000); 3 Clin Invest, 109(3): 337-46 (2002); and US 20090124007 A1.

In other embodiments, the delivery system disclosed herein may use pluripotent stem cells (e.g., human pluripotent stem cells) as the starting material for producing EPCs. As used herein, "pluripotent" or "pluripotency" refers to the potential to form all types of specialized cells of the three germ layers (endoderm, mesoderm, and ectoderm); and is to be distinguished from "totipotent" or "totipotency", that is the ability to form a complete embryo capable of giving rise to offsprings. As used herein, "human pluripotent stem cells" (hPSC) refers to human cells that have the capacity, under appropriate conditions, to self-renew as well as the ability to form any type of specialized cells of the three germ layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human embryonic stem (hES) cells. The various methods described herein may utilize hPS cells from a variety of sources. For example, hPS cells suitable for use may have been obtained from developing embryos by use of a nondestructive technique such as by employing the single blastomere removal technique described in e.g. Chung et al (2008), further described by Mercader et al. in Essential Stem Cell Methods (First Edition, 2009). Additionally or alternatively, suitable hPS cells may be obtained from established cell lines or may be adult stem cells.

In some aspects, the pluripotent stem cells for use according to the disclosure may be human embryonic stem cells (hESs). Various techniques for obtaining hES cells are known to those skilled in the art. In some instances, the hES cells for use according to the present disclosure are ones, which have been derived (or obtained) without destruction of the human embryo, such as by employing the single blastomere removal technique known in the art. See, e.g., Chung et al., Cell Stem Cell, 2(2):113-117 (2008), Mercader et al., Essential Stem Cell Methods (First Edition, 2009). Suitable hES cell lines can also be used in the methods disclosed herein. Examples include, but are not limited to, cell lines SA167, SA181, SA461 (Cellartis AB, Goteborg, Sweden) which are listed in the NIH stem cell registry, the UK Stem Cell bank and the European hESC registry and are available on request. Other suitable cell lines for use include those established by Klimanskaya et al., Nature 444:481-485 (2006), such as cell lines MA01 and MA09, and Chung et al., Cell Stem Cell, 2(2):113-117 (2008), such as cell lines MA126, MA127, MA128 and MA129, which all are listed with the International Stem Cell Registry (assigned to Advanced Cell Technology, Inc. Worcester, MA, USA).

Alternatively, the pluripotent stem cells for use in the methods disclosed herein may be induced pluripotent stem cells (iPSCs) such as human iPSCs. As used herein "hiPS cells" refers to human induced pluripotent stem cells. hiPS cells are a type of pluripotent stem cells derived from non-pluripotent cells—typically adult somatic cells—by induction of the expression of genes associated with pluripotency, such as SSEA-3, SSEA-4, TRA-1-60, TRA-1-81, Oct-4, Sox2, Nanog and Lin28. Various techniques for obtaining such iPSC cells have been established and all can be used in the present disclosure. See, e.g., Takahashi et al., Cell 131(5):861-872 (2007); Zhou et al., Cell Stem Cell. 4(5):381-384 (2009); Yu and Thomson in Essentials of Stem Cell Biology (2nd Edition, Chapter 4)]. It is also envisaged that the EPCs may also be derived from other pluripotent stem cells such as adult stem cells, cancer stem cells or from other embryonic, fetal, juvenile or adult sources.

In some embodiments, the delivery system of the disclosure comprises a population of EPCs. As used herein, a "population" of cells refers to a group of at least 2 cells, e.g. 2 cells, 3 cells, 4 cells, 10 cells, 100 cells, 1000 cells, 10,000 cells, 100,000 cells or any value in between, or more cells. Optionally, a population of cells can be cells which have a common origin, e.g. they can be descended from the same parental cell, they can be clonal, they can be isolated from or descended from cells isolated from the same tissue, or they can be isolated from or descended from cells isolated from the same tissue sample. Preferably, the population of EPCs is substantially purified. As used herein, the term "substantially purified" means a population of cells substantially homogeneous for a particular marker or combination of markers. By substantially homogeneous is meant at least 80%, at least 85%, at least 90%, at least 95%, at least 96%, at least 97%, at least 98%, at least 99% or more homogeneous for a particular marker or combination of markers.

(a) Labeling of EPCs

As shown herein, the disclosed delivery system comprises EPCs labeled with an imaging agent or therapeutic agent and utilized as theranostic tools, i.e. for tumor diagnosis/detection/imaging and as a targeted therapy.

Current strategies using surface markers as imaging targets in cancer are inadequate since different tumor clones express diverse surface markers; therefore, a more universal strategy that does not depend on the surface markers is an urgent need. In some embodiments, the delivery system, utilizes EPCs labeled with trackable imaging agent as a universal marker for imaging of different types of cancer independent of their surface markers expression.

As used herein the term "labeling" refers to the process of culturing EPCs in the presence of an imaging agent or therapeutic agent for a sufficient amount of time such that the imaging or therapeutic agent is retained on or within the EPCs. Accordingly, EPCs labeled with an imaging or therapeutic agent will have a higher concentration of the imaging or therapeutic agent relative to EPCs cultured in the absence of the imaging or therapeutic agent. In another aspect, the EPCs may be genetically labeled with and imaging or therapeutic agent. A genetically labeled EPC refers to the introduction of an exogenous nucleic acid sequence or peptide sequence which may then be detected (e.g., florescent peptides, heavy and/or light chain ferritin) or results in gene-loaded EPCs with anti-cancer effects (e.g, thymidine kinases, cytosine deaminases, intracellular antibodies, telomereases, caspases, DNases). Genetically labeled EPCs can be generated using standard techniques known in the art i.e., transfection or transduction.

In some embodiments, EPCs may be labeled with any suitable imaging agent known in the art, for example, the imaging agent is any molecule in which a signal may be assayed. In general, an imaging agent may include luminescent molecules, chemiluminescent molecules, fluorochromes, fluorophores, colored molecules, radioisotopes, radionuclides, cintillants, massive labels such as a metal atom (for detection via mass changes), biotin, avidin, streptavidin, protein A, protein G, antibodies or fragments thereof, Grb2, polyhistidine, $Ni^{2+}$, Flag tags, myc tags, heavy metals, enzymes, alkaline phosphatase, peroxidase, luciferase, electron donors/acceptors, acridinium esters, and colorimetric substrates. Many assays and detection schemes are well known to one of skill in the art for various reporter molecules and can be utilized with the disclosure. In some embodiments, the imaging agents including, but not limited to, fluorophores, nanoparticles, radionuclides, bioluminescence imaging agents, MRI contrast agents, and X-ray/CT contrast agents.

Non-limiting examples of fluorophores include fluorescent dyes, immunolabeling, and fluorescent fusion proteins, all of which can provide a means to selectively mark structures and proteins within the cell, allowing you to see them more easily when you image. In some embodiments, the imaging agent is a near-infra-red imaging agent. In an exemplary embodiment, the imaging agent is LS-542.

Owing to inherent magnetic, optical or acoustic attributes, nanoparticles as imaging agents can be detected by corresponding imaging modalities in living subjects at a high spatial and temporal resolution. These features allow implanted cells to be separated from host cells; and have advantages over traditional histological methods, as they permit non-invasive, real-time tracking in vivo. Examples of nanoparticles include, but are not limited to, iron oxide nanoparticles (IONPs), gadolinium hexanedione nanoparticles (GdH-NPs), liposomal-based nanoparticle, Quantum dots (QDs), upconversion nanoparticles, silica nanoparticles, carbon nanotubes, gold nanorods, PEGylated-PLGA nanoparticles and the like. In one aspect, the imaging agent is a PEGylated-PLGA nanoparticles-loaded with detectable moiety.

Non-limiting examples of radionucleotides include Yttrium-90, Radium-223, Actinium-225, Bismuth-213, Lead-212, Astatine-211, Copper-64, Fluorine-18, Gallium-68, Copper-64, and Zirconium-89. In some embodiments, the imaging agent is a Gallium-68. In an exemplary embodiment, the imaging agent is 18F-Fluorodeoxyglucose. In another exemplary embodiment, the imaging agent is Zirconium-89.

Examples of bioluminescence imaging agents include, but are not limited to, firefly luciferase, renilla luciferase, gaussia luciferase, and bacterial luciferase.

In yet another non-limiting example, the imaging agent contains an epitope that can be bound by an antibody. A labeled form of the antibody or a secondary antibody that binds the antibody that in turn binds the imaging agent and can then be used to assay the presence of the antibody. One of skill in the art can readily determine a detection scheme useful for visualizing an immunological epitope with a specific antibody.

Due to the unique physicochemical properties of the imaging agents it is appreciated that to allow visualization of the delivery system and thereby cancer cells in vivo or in vitro, different molecular imaging modalities or assays may be used, such as, magnetic resonance imaging (MRI), radionuclide imaging (positron emission tomography (PET) and single-photon emission computed tomography (SPECT)), optical imaging, flow cytometry, and the like. In a non-limiting example, the assay may be a physical detection such as spectrophotometric detection of the imaging agent.

In some embodiments, EPCs may be labeled with any suitable therapeutic agent known in the art to treat a cancer or tumor or a symptom resulting therefrom. Non-limiting examples of therapeutic agents include anti-neoplastic agents, photodynamic therapy pro-drugs, boron-containing compounds, mitotic inhibitors, immune-related agents, biological response modifiers, vitamins, peptides, anti-inflammatories, and radioactive particles. In some embodiments, non-limiting examples of a therapeutic agent may include proteasome inhibitors, histone deacetylase inhibitors, chemotherapeutic agents, immunomodulating agents, or other agents that may be toxic to or kill cancer cells. Non-limiting examples of proteasome inhibitors may include bortezomib, carfilzomib, marizomib, ixazomib, or MLN9708. Non-limiting examples of a histone deacetylase inhibitor may be panobinostat, vorinostat, zolinza, romidepsin, or Istodax. Non limiting examples of chemotherapeutic agents may be doxorubicin, melphalan, vincristine, cyclophosphamide, etoposide, or bendamustine. Non-limiting examples of immunomodulating agents may be thalidomide, lenalidomide, or pomalidomide.

Non-limiting examples of antineoplastic agents include bortezomib, platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, monomethyl auristatin E (MMAE), drug maytansinoids (e.g. DM1), procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon α-2a, interferon α-2b, teniposide (VM-26), vinblastine sulfate (VLB), vincristine sulfate, bleomycin sulfate, hydroxyurea, procarbazine, and dacarbazine.

Photodynamic therapy (PDT), the concept of cancer treatment through the selective uptake of a light-sensitive agent followed by irradiation to a specific wavelength. Examples of photodynamic therapy pro-drugs include but are not limited to porphyrins, chlorins and dyes. Examples include aminolevulinic acid (ALA), Silicon Phthalocyanine Pc 4, m-tetrahydroxyphenylchlorin (mTHPC) and mono-L-aspartyl chlorin e6 (NPe6). Photodynamic therapy pro-drugs commercially available for clinical use include Allumera, Photofrin, Visudyne, Levulan, Foscan, Metvix, Hexvix, Cysview and Laserphyrin, with others in development, e.g. Antrin, Photochlor, Photosens, Photrex, Lumacan, Cevira, Visonac, BF-200 ALA, Amphinex and Azadipyrromethenes. In an exemplary embodiment, the therapeutic agent is titanocene.

Boron Neutron Capture Therapy (BNCT) is a radiation science which is emerging as a hopeful tool in treating cancer, by selectively concentrating boron compounds in tumor cells and then subjecting the tumour cells to epithermal neutron beam radiation. Non-limiting examples of boron-containing compounds include boric acid and some of its derivatives, boronophenylalanine (BPA), borocaptate Sodium (BSH), BPA-fructose complex, and $^{18}$F-BPA.

Examples of mitotic inhibitors include but are not limited to mitotic etoposide, colchicine, and the vinca alkaloids.

Non-limiting examples of immune-related agents include but are not limited to immune serums, antitoxins, antivenoms bacterial vaccines, viral vaccines, rabies prophylaxis products.

Examples of biological response modifiers include but are not limited cytokines, muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine Non-limiting examples of vitamins include cyanocobalamin neinoic acid, retinoids and derivatives such as retinol palmitate, and α-tocopherol.

Examples of peptides include but are not limited to manganese super oxide dismutase; enzymes such as alkaline phosphatase Non-limiting examples of anti-inflammatories diflunisal, ibuprofen, indomethacin, meclofenamate, mefenamic acid, naproxen, oxyphenbutazone, phenylbutazone, piroxicam, sulindac, tolmetin, aspirin and salicylates Examples of radioactive particles or ions include but are not limited to Actinium, lead212, radium, strontium, iodide rhenium, yttrium, and radiopharmaceuticals, such as radioactive iodine, copper and phosphorus products.

A pharmaceutical composition of the disclosure including the delivery system disclosed herein may also comprise one or more nontoxic pharmaceutically acceptable carriers, adjuvants, excipients, and vehicles as desired. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with a cell delivery system of the invention, use thereof in the compositions is contemplated. Supplementary active compounds may also be incorporated into the compositions.

A pharmaceutical composition of the invention may be formulated to be compatible with its intended route of administration. Suitable routes of administration may include parenteral, oral, pulmonary, transdermal, transmucosal, and rectal administration. The term parenteral, as used herein, includes subcutaneous, intravenous, intramuscular, intrathecal, or intrasternal injection, or infusion techniques.

Solutions or suspensions used for parenteral, intradermal, or subcutaneous application may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH may be adjusted with acids or bases, such as hydrochloric acid or sodium hydroxide. The parenteral preparation may be enclosed in ampoules, disposable syringes or multiple dose vials made of glass or plastic.

Oral compositions generally may include an inert diluent or an edible carrier. Oral compositions may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents and/or adjuvant materials may be included as part of the composition. The tablets, pills, capsules, troches, and the like, may contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressured container or dispenser which contains a suitable propellant, e.g., a gas such as carbon dioxide, or a nebulizer.

In preferred embodiments, a pharmaceutical composition of the invention is formulated to be compatible with parenteral administration. For instance, pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.), or phosphate buffered saline (PBS). In exemplary embodiments, a pharmaceutical composition of the invention is formulated with phosphate buffered saline (PBS).

In all cases, a composition may be sterile and may be fluid to the extent that easy syringe ability exists. A composition may be stable under the conditions of manufacture and storage, and may be preserved against the contaminating action of microorganisms such as bacteria and fungi. The carrier may be a solvent or dispersion medium containing, for example, water, ethanol, polyol (for example, glycerol, propylene glycol, and liquid polyetheylene glycol, and the like), and suitable mixtures thereof. The proper fluidity may be maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it may be preferable to include isotonic agents, for example, sugars, polyalcohols such as mannitol, sorbitol, or sodium chloride, in the composition. Prolonged absorption of the injectable compositions may be brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Systemic administration may also be by transmucosal or transdermal means. For transmucosal or transdermal administration, penetrants appropriate to the barrier to be permeated are used in the formulation. Such penetrants are generally known in the art, and may include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds may also be prepared in the form of suppositories (e.g., with conventional suppository bases such as cocoa butter and other glycerides) or retention enemas for rectal delivery.

In one embodiment, a delivery system of the present disclosure may be prepared with carriers that will protect the imaging to therapeutic agent against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art.

Additional formulations of pharmaceutical delivery systems may be in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980). Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. A suitable pharmaceutically acceptable carrier to maintain optimum stability, shelf-life, efficacy, and function of the delivery system would be apparent to one of ordinary skill in the art.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

II. Methods

Also provided by the disclosure is a method of treating cancer in a subject in need by administration of a therapeutically effective amount of a composition comprising the delivery system labeled with a therapeutic agent, such that the cancer is killed. Accordingly, the disclosure provides a method of killing a cancer cell in a subject in need thereof.

In some embodiment, the disclosure provides methods of detecting a cancer cell in a subject having or suspected of having cancer or a tumor. In other embodiments, the disclosure provides method of monitoring cancer progression or the efficacy of a cancer therapeutic.

In an aspect, the present invention encompasses administering a therapeutically effective amount of a delivery system labeled with an imaging agent or therapeutic agent to a subject in need thereof. Suitable delivery systems are described in detail in Section I. As used herein, the phrase "a subject in need thereof" refers to a subject in need of preventative or therapeutic treatment. A subject may be a rodent, a human, a livestock animal, a companion animal, or a zoological animal. In one embodiment, a subject may be a rodent, e.g., a mouse, a rat, a guinea pig, etc. In another embodiment, a subject may be a livestock animal. Non-limiting examples of suitable livestock animals may include pigs, cows, horses, goats, sheep, llamas and alpacas. In still another embodiment, a subject may be a companion animal. Non-limiting examples of companion animals may include pets such as dogs, cats, rabbits, and birds. In yet another embodiment, a subject may be a zoological animal. As used herein, a "zoological animal" refers to an animal that may be found in a zoo. Such animals may include non-human primates, large cats, wolves, and bears. In a preferred embodiment, a subject is a mouse. In another preferred embodiment, a subject is a human.

In another aspect, the present disclosure provides a method of killing a cancer, the method comprising contacting the cancer cell with an effective amount of a delivery system labeled with a therapeutic agent as disclosed herein. In various embodiments, contact with the delivery system results increased cancer cell death relative to cancer cells in the absence of contact with the delivery system.

Contacting a cancer cell with an effective amount of a delivery system involves admixing the delivery system and the cancer cell for a period of time sufficient to allow the delivery system to migrate to the cancer cell and increase the concentration of the therapeutic agent in and/or around the cancer cell. This may occur in vitro or ex vivo or in vivo. The term "effective amount", as used herein, means an amount that leads to measurable effect, e.g., cancer cell death. The effective amount may be determined by using the methods known in the art and/or described in further detail in the examples.

In another aspect, the present disclosure provides a method for treating a subject having a cancer or tumor. The method comprises administering to the subject a therapeutically effective amount of a delivery system labeled with a therapeutic agent to the subject. Suitable delivery systems are described in detail in Section I.

In still another embodiment, the present disclosure provides a method of detecting a cancer cell in a subject having or suspected of having a cancer or tumor. The method comprises administering to the subject a delivery system labeled with an imaging agent and measuring the signal emitted from the imaging agent. In some embodiments, the signal of the imaging agent is compared to a signal of the imaging agent in a control. In some embodiments the method further comprises classifying the subject as having or not having cancer. In some embodiments, the subject is classified as having cancer if the signal of the imaging agent is increased relative to a healthy control. In some embodiments, the subject is classified as not having cancer if the signal of the reporter molecule is the same or decreased relative to a healthy control.

Additionally, the present disclosure provides a method for monitoring cancer or tumor progression or response to a therapeutic agent in a subject. As used herein, subjects who respond to treatment are said to have benefited from treatment. Responses to treatment are measured in clinical practice using tests well known in the art and are intended to refer to specific parameters measured during clinical trials and in clinical practice by a skilled artisan. For example, a method of administering the delivery system labeled with an imaging agent and measuring a signal from the imaging agent may be performed prior to initiation of treatment. Then at a later time, a method of administering the delivery system labeled with an imaging agent and measuring a signal from the imaging agent may be used to determine the response to treatment over time. For example, a method of administering the delivery system labeled with an imaging agent and measuring a signal from the imaging agent may be performed on the subject days, weeks, months or years following initiation of treatment. Accordingly, a method of administering the delivery system labeled with an imaging agent and measuring a signal from the imaging agent may be used to follow a subject receiving treatment to determine if the subject is responding to treatment. If the signal of the imaging agent is decreased relative to a sample prior to treatment, then the subject may be responding to treatment. If the signal of the imaging agent increases or remains the same relative to a sample prior to treatment, then the subject may not be responding to treatment. These steps may be repeated to determine the response to therapy over time.

Any suitable control sample known in the art may be used for the methods described herein. For example, a suitable control may be the signal of a imaging agent from a subject or group of subjects of the same species that has no detectable cancer or tumor. In another example, a suitable control may be the signal of a imaging agent in a subject or group of subjects of the same species that has detectable cancer or tumor as measured via standard methods. In another example, a suitable control may be a measurement of the imaging agent in a reference sample obtained from the same subject. The reference sample comprises the same type of sample as the test sample, and may or may not be obtained from the subject when cancer was not suspected. A skilled artisan will appreciate that it is not always possible or desirable to obtain a reference sample from a subject when the subject is otherwise healthy. For example, in an acute setting, a reference sample may be the first sample obtained from the subject at presentation. In another example, when monitoring the effectiveness of a therapy, a reference sample may be a sample obtained from a subject before therapy began. In such an example, a subject may have suspected cancer but may not have other symptoms of cancer or the subject may have suspected cancer and one or more other symptom of cancer.

In some embodiments, the methods disclosed herein may further comprise obtaining a biological sample from a subject and assaying the biological sample to measure a signal from an imaging agent as disclosed herein. As used herein, the term "biological sample" may be, in non-limiting examples, a biological fluid, a tissue, a tissue homogenate, cells, a cellular lysate, a tissue or cell biopsy, skin cells, tumor or cancer cells, or any combination thereof. Any biological sample containing the disclosed delivery system is suitable. Numerous types of biological samples are known in the art. In some embodiments, the biological sample is a tissue sample such as a tissue biopsy. In one aspect, the biopsied tissue may be processed into individual cells or an explant, or processed into a homogenate, a cell extract, a membranous fraction, or a ceramide extract. In other embodiments, the sample may be a bodily fluid. Non-limiting examples of suitable bodily fluids include blood, plasma, serum, urine, and saliva. In a specific embodiment, the biological sample is blood, plasma, or serum. In a specific embodiment, the biological sample is plasma. The fluid may be used "as is", the cellular components may be isolated from the fluid, or a fraction may be isolated from the fluid using standard techniques.

In some embodiments, the methods disclosed herein may further comprise the steps of obtaining a population of endothelial progenitor cells (EPCs). In one aspect, the population of EPCs is obtained from the subject. In some embodiments, the EPCs are culture in contact with an imaging agent or therapeutic agent under conditions sufficient for labeling the EPCs with the agent. In some embodiments, the labeled EPC are then administered to the subject.

In some embodiments, the EPCs are primed prior to administration to a subject. As used herein the term "priming" or "primed" refers to culturing the EPCs in a medium comprising components which improve EPCs homing to cancer or tumor cells relative to EPCs that were culture in the absence of said medium. In a non-limiting example, EPCs may be culture in a medium comprising chemokines and cytokines secreted by cancer cells. Accordingly, the EPCs may be cultured in with hypoxia- and/or cancer-conditioned media. Hypoxia refers to low oxygen conditions (e.g., in normoxia is about 21% $O_2$ and hypoxia is about 1% $O_2$). A conditioned medium is a medium that was in contact with certain cells or under specific conditions for a sufficient amount of time to contain components secreted or fragments of said cells. In non-liming examples, cytokines present in a medium used to prime EPCs may include pro-angiogenic factors, VEGF, SDF-1, IL-8, GRO-a, CCL5, CCL2, and/or CXCL11.

One of skill in the art will recognize that the amount and concentration of the composition administered to a subject will depend in part on the subject and the reason for the administration. Methods for determining optimal amounts are known in the art. Generally, a safe and effective amount of a delivery system composition is, for example, that amount that would cause the desired therapeutic effect in a subject while minimizing undesired side effects. In various embodiments, an effective amount of a delivery system composition described herein can substantially inhibit cancer progression, slow the progress of cancer, or limit the development of cancer.

The treatment of cancer with a delivery system of the present disclosure may be in combination with one or more therapies selected from antibody therapy, chemotherapy, cytokine therapy, dendritic cell therapy, gene therapy, hormone therapy, radiotherapy, laser light therapy, and radiation therapy.

The administration of a delivery system or a population of EPCs of the present disclosure can be carried out by aerosol inhalation, injection, ingestion, transfusion, implantation or transplantation. The delivery system compositions described herein, may be administered to a subject subcutaneously, intradermally, intratumorally, intranodally, intramedullary, intramuscularly, by intravenous or intralymphatic injection, or intraperitoneally. In one embodiment, the cell compositions of the present disclosure are preferably administered by intravenous injection.

The administration of a delivery system or a population of EPCs can consist of the administration of $10^4$-$10^9$ cells per kg body weight, preferably $10^5$ to $10^6$ cells/kg body weight including all integer values of cell numbers within those ranges.

Compositions of the invention are typically administered to a subject in need thereof in an amount sufficient to provide a benefit to the subject. This amount is defined as a "therapeutically effective amount." A therapeutically effective amount may be determined by the efficacy or potency of the particular composition, the disorder being treated, the duration or frequency of administration, the method of administration, and the size and condition of the subject, including that subject's particular treatment response. A therapeutically effective amount may be determined using methods known in the art, and may be determined experimentally, derived from therapeutically effective amounts determined in model animals such as the mouse, or a combination thereof. Additionally, the route of administration may be considered when determining the therapeutically effective amount. In determining therapeutically effective amounts, one skilled in the art may also consider the existence, nature, and extent of any adverse effects that accompany the administration of a particular compound in a particular subject.

When used in the treatments described herein, a therapeutically effective amount of a composition can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to, for example, reduce cancer progression.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Shawl (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a delivery system composition can occur as a single event or over a time course of treatment. For example, a delivery system composition can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities cancer.

A delivery system of the disclosure can be administered simultaneously or sequentially with another agent, such as an antibiotic, an anti-inflammatory, or another agent. For example, a delivery system of the disclosure can be administered simultaneously with another agent, such as an antibiotic or an anti-inflammatory.

In preferred aspects, a method of the invention is used to treat a neoplasm or cancer. The neoplasm may be malignant or benign, the cancer may be primary or metastatic; the neoplasm or cancer may be early stage or late stage. A cancer or a neoplasm may be treated by delivering delivery system of the disclosure labeled with a therapeutic agent to at least one cancer cell in a subject. The cancer or neoplasm may be treated by slowing cancer cell growth or killing cancer cells.

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

In some aspects, the delivery system of the disclosure of may treat a cancer or a neoplasm by delivering a therapeutic agent to a cancer cell in a subject in vivo. Non-limiting examples of neoplasms or cancers that may be treated with a method of the invention may include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/ carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-cell lymphoma (cutaneous), T-cell leukemia and lymphoma, testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, or Wilms tumor (childhood).

In other aspects, delivery system of the disclosure may deliver a therapeutic agent to a cancer cell in vitro. A cancer cell may be a cancer cell line cultured in vitro. In some alternatives of the embodiments, a cancer cell line may be a primary cell line that is not yet described. Methods of preparing a primary cancer cell line utilize standard techniques known to individuals skilled in the art. In other alternatives, a cancer cell line may be an established cancer cell line. A cancer cell line may be adherent or non-adherent, or a cell line may be grown under conditions that encourage adherent, non-adherent or organotypic growth using standard techniques known to individuals skilled in the art. A cancer cell line may be contact inhibited or non-contact inhibited.

In some embodiments, the cancer cell line may be an established human cell line derived from a tumor. Non-limiting examples of cancer cell lines derived from a tumor may include the MM cell lines MM.1S, H929, and RPMI, osteosarcoma cell lines 143B, CAL-72, G-292, HOS, KHOS, MG-63, Saos-2, or U-2 OS; the prostate cancer cell lines DU145, PC3 or Lncap; the breast cancer cell lines MCF-7, MDA-MB-438 or T47D; the myeloid leukemia cell line THP-1, the glioblastoma cell line U87; the neuroblastoma cell line SHSY5Y; the bone cancer cell line Saos-2; the colon cancer cell lines WiDr, COLO 320DM, HT29, DLD-1, COLO 205, COLO 201, HCT-15, SW620, LoVo, SW403, SW403, SW1116, SW1463, SW837, SW948, SW1417, GPC-16, HCT-8, HCT 116, NCI-H716, NCI-H747, NCI-H508, NCI-H498, COLO 320HSR, SNU-C2A, LS 180, LS 174T, MOLT-4, LS513, LS1034, LS411 N, Hs 675.T, CO 88BV59-1, Co88BV59H21-2, Co88BV59H21-2V67-66, 1116-NS-19-9, TA 99, AS 33, TS 106, Caco-2, HT-29, SK-CO-1, SNU-C2B or SW480; B16-F10, RAW264.7, the F8 cell line, or the pancreatic carcinoma cell line Panc1. In an exemplary embodiment, a method of the disclosure may be used to contact a cell of a MM cell line.

III. Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to EPCs, priming media, therapeutic agents, or imaging agents. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

EXAMPLES

Example 1: Isolation and Tumor Homing of EPCs In Vitro

Angiogenesis plays a pivotal role in tumor progression (56), and is governed by an imbalance between pro-angiogenic and anti-angiogenic factors, causing an "angiogenic switch" (de la Puente et al., Clinical Cancer Research, 19(13):3360-8 (2013)). Besides sprouting from pre-existing endothelial cells in the tumor bed, cancer cells utilize other methods of vessel growth, in which angiogenesis is facilitated through recruitment of EPCs to the tumor vascular bed (Shi et al., Blood. 15; 92(2):362-7 (1998); Liu et al., Frontiers in bioscience, 17:2559-65(2012)). EPCs are a subtype of stem cells with high proliferative potential capable of differentiating into mature endothelial cells and contributing to neo-angiogenesis (Peichev et al., Blood. 95(3):952-8 (2000)). In addition, tumor-derived paracrine signals activate the bone marrow (BM) compartment, resulting in the mobilization and recruitment of EPCs to the tumor bed (Urbich et al., Circulation research, 20; 95(4):343-53 (2004)). In this process, EPCs are attracted by chemokine gradients secreted by cancer cells (Aicher et al., Hypertension, 45(3):321-5 (2005)), to facilitate their homing to tumor sites where they participate in neo-angiogenesis (Li et al., Microvascular research, 79(3):207-16 (2010)). Therefore, the goal of this study was to examine potential sources for endothelial progenitor cell (EPC) isolation and to test the tumor homing ability of EPCs in vitro and in vivo.

Methods

Isolation of EPCs from Cord Blood, Bone Marrow and Fat Tissue

Mononuclear cells were isolated from cord blood, bone marrow or fat tissue by tissue homogenization followed by red—cell lysis, spin down and resuspended in PBS. Then, cells were stained with antibodies against CD31, CD34, Cd105, and VEGFR2 on ice for one hour, washed, and analyzed by flow cytometry.

In Vitro Assay EPC Migration Over Time

Using Boyden chamber a chemotaxis assay in vitro was performed using EPCs derived from cord blood towards non-conditioned media, H929-conditioned media, or using HUVECs towards H929-conditioned media. The migrated EPCs were counted in the lower Boyden chamber by flow cytometry after 2, 6, 8, 12 and 24 hours.

In Vitro Assay EPC Migration Correlates with Tumor Burden

Figure 3A:
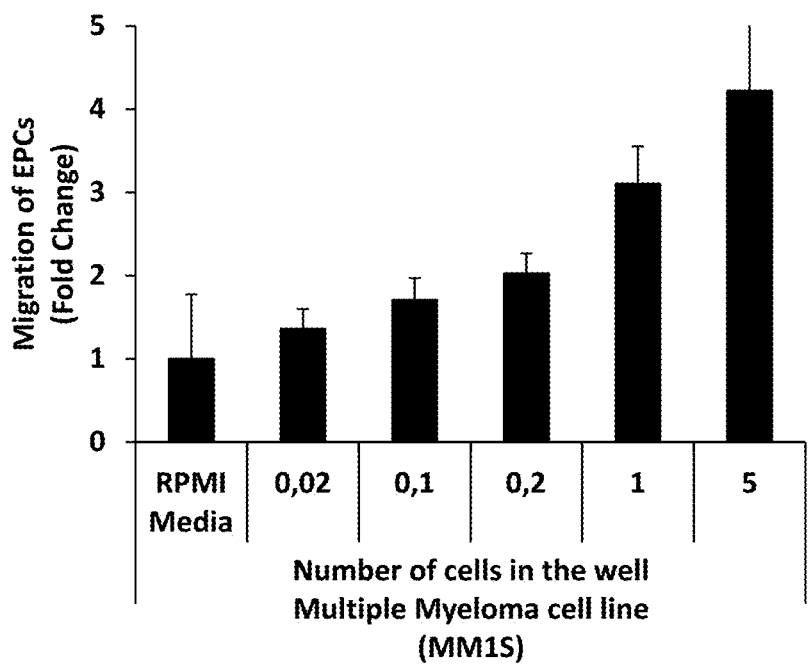
FIG. 3A-B include bar graphs depicting the migration of EPCs to increasing numbers of tumor cells.
Figure 3B:
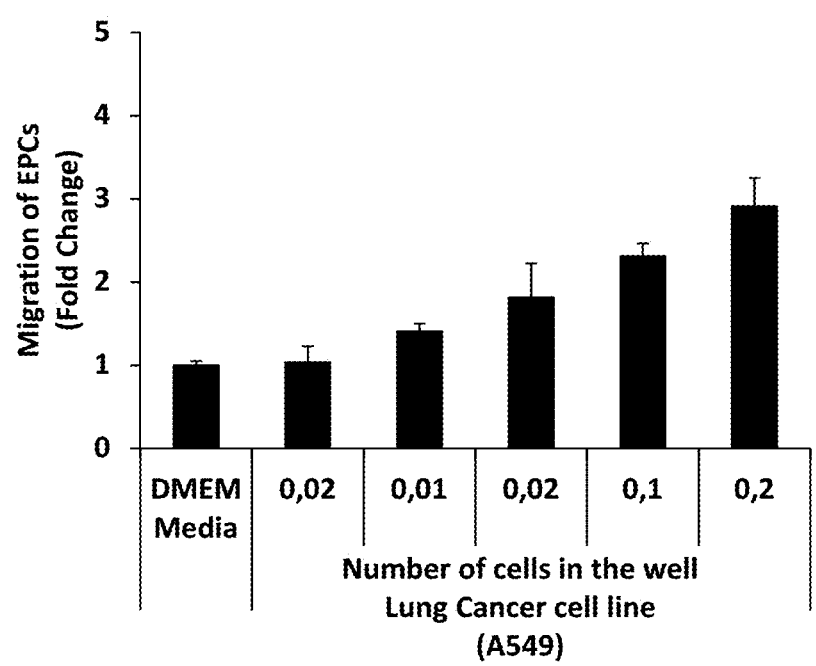

Using Boyden chamber a chemotaxis assay in vitro was performed using HUVECs towards non-conditioned media RPMI, and increasing numbers of MM cells in the lower chamber (FIG. 3A); or towards non-conditioned media DMEM, and increasing numbers of lung cancer cells in the lower chamber (FIG. 3B). The migrated HUVECs were counted in the lower Boyden chamber by flow cytometry after 24 hours.

EPCs Migrate to Different Tumor Types In Vitro

Using a Boyden chamber a chemotaxis assay in vitro was performed utilizing media-derived from MM cell lines (MM.1S, H929, and OPM1), lymphoma cell line (BCWM1), and CML cell line (K562), which were cultured at $1 \times 10^6$ cells per 1 mL of RPMI1640 media for 24 hours, as well as solid tumors including lung (A549), pancreas (BxPC3) and glioma (U87) cell lines, which were cultured at $0.1 \times 10^6$ cells per 1 mL of DMEM media for 24 hours were compared to non-conditioned media. The migrated HUVECs were counted in the lower Boyden chamber by flow cytometry after 24 hours.

Figure 1B:
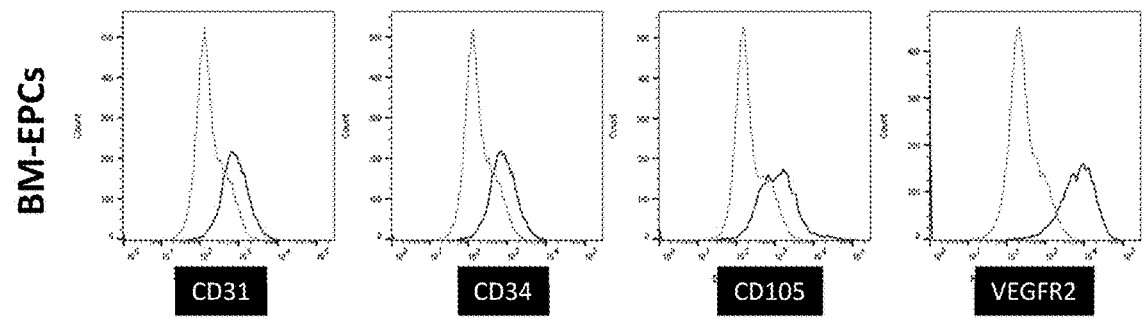
Figure 1C:
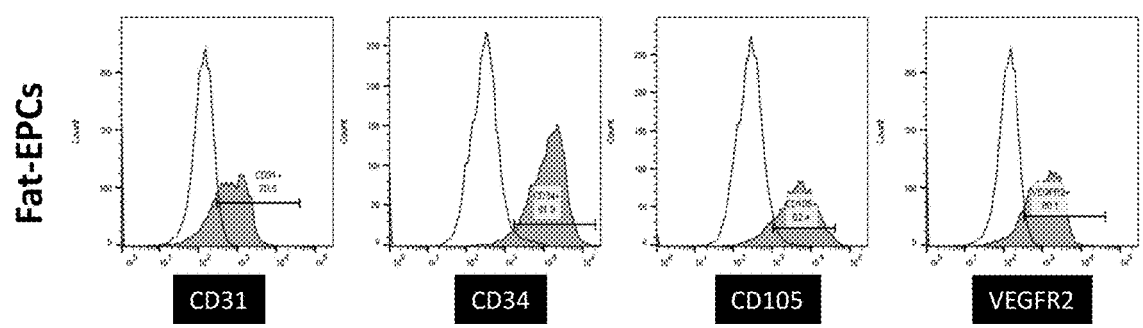

Results (i) EPCs Migrate to Both Hematological and Solid Tumors and Migration Correlates with Tumor Burden and Time To elucidate the ability to isolate EPCs from various tissues flow-cytometry was used to identify the expression of EPC markers (CD31+/CD34+/CD105+/VEGFR2+) on EPCs isolated from cord blood (FIG. 1A), bone marrow (BM) (FIG. 1B) and fat tissue (FIG. 1C). FIG. 1A-1C shows EPCs can be isolated from cord blood, bone marrow (BM) or fat tissue. EPCs are distinguished at different stages of differentiation through CD marker expression; the bone marrow EPCs express stem cell markers CD133 and CD34, the circulating EPCs express more mature markers including CD31, CD146, CD144, whereas terminally differentiated ECs are characterized by VEGFR-2, CD31, CD146, VE-cadherin, eNOS, and vWF.

The prevalence of EPCs in the bone marrow (BM) and the peripheral blood (PB) of MM patients and healthy subjects by flow cytometry by using EPCs biomarkers (CD34+ CD31+) was previously tested. It was found that EPCs were about three times more prevalent in the BM ($p<0.001$) and the PB ($p=0.01$) of MM patients compared to healthy subjects, with about 6-fold higher percentile of EPCs in the BM compared to PB in healthy subjects and about 2, 3-fold higher percentile of EPCs in the BM compared to PB in MM patients (not shown). It was also demonstrated that HUVECs demonstrated a 3-fold higher rate of chemotaxis to the BM supernatants from MM patients compared to healthy subjects ($p<0.02$) in a chemotaxis assay in vitro using Boyden chamber (not shown). These results indicated that EPCs play an important role in tumor progression in MM, and that there is continuous cell trafficking of EPCs between the BM and PB.

Figure 2:
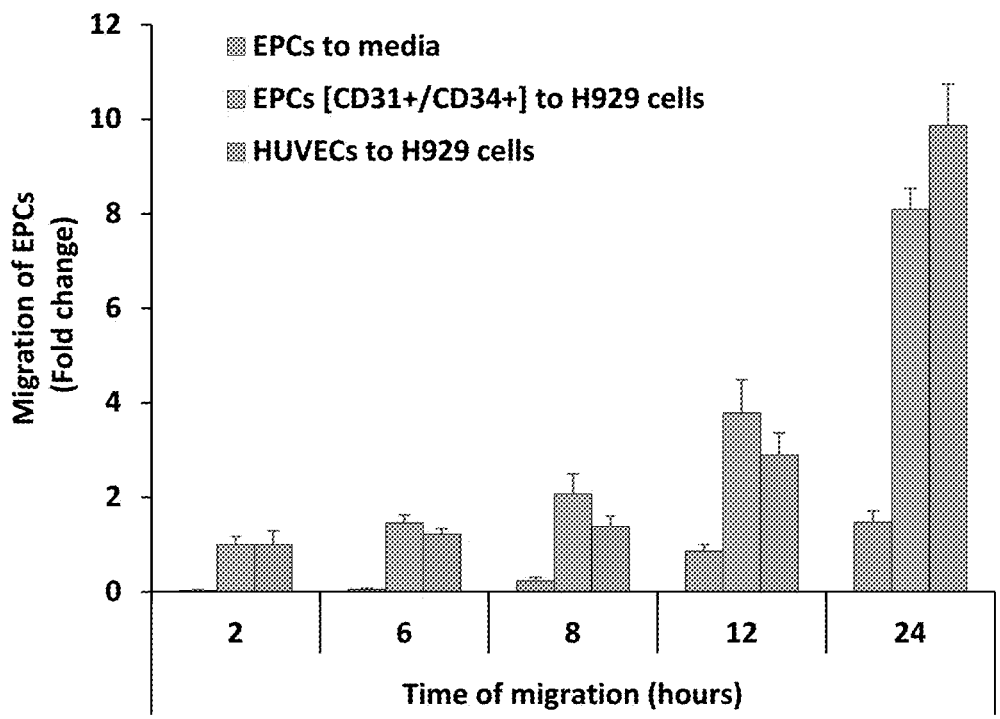
FIG. 2 is a bar graph showing EPCs migrate specifically to tumor cells over time.

Following these findings, and since EPCs play a crucial role in the neo-angiogenesis in all types of tumors, the ability of EPCs to migrate to conditioned media in vitro was investigated. EPCs from different sources including cord-blood-derived endothelial cells (CD31+/CD34+), and human umbilical vein endothelial cells—HUVECs (CD31+/CD34+) migrated more to tumor (myeloma H929 cells) than to non-conditioned media, in a time-dependent manner (FIG. 2). These results demonstrated that tumor cells attract and induce specific migration of EPCs over time.

Figure 4:
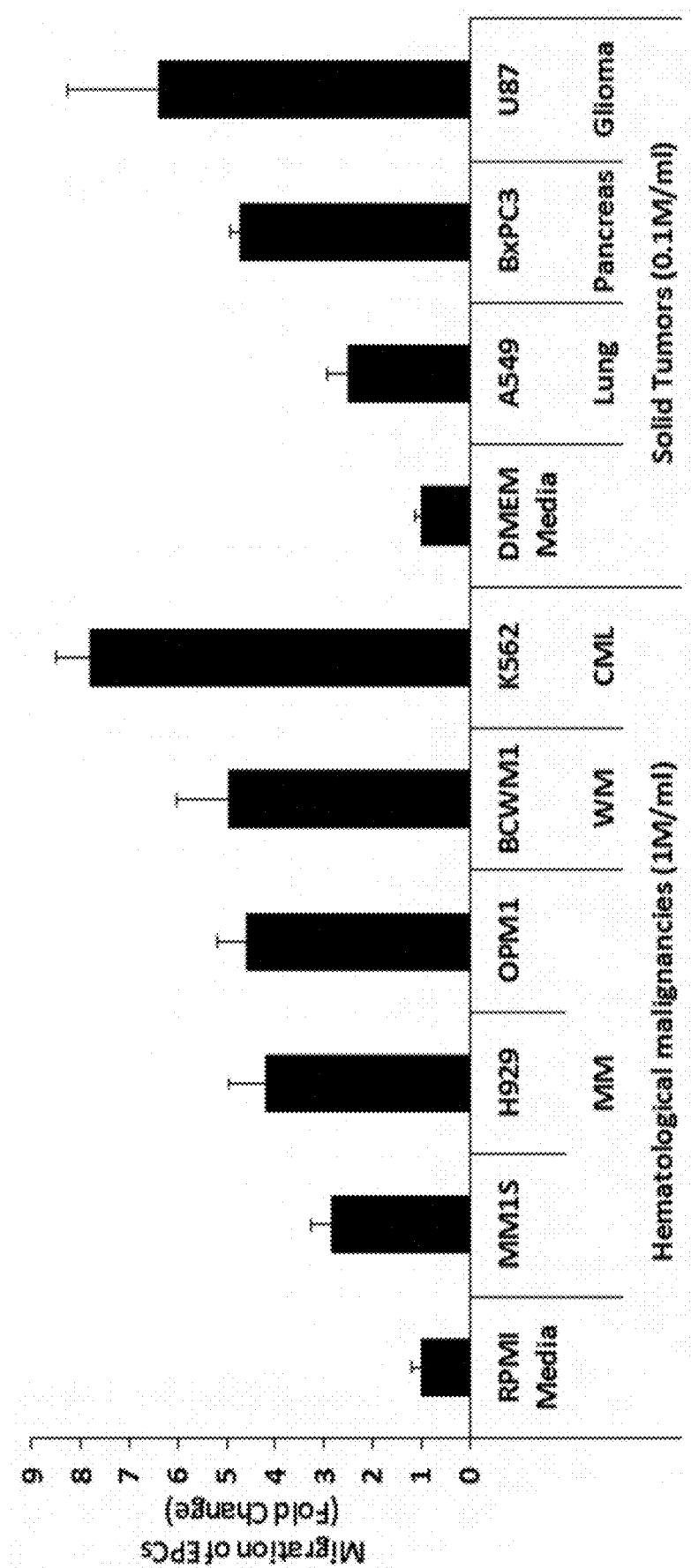
FIG. 4 is a bar graph depicting EPCs migrate to different tumor types in vitro including hematological malignancies (multiple myeloma MM.1S, H929, and OPM1; Waldenstrom macroglobulinemia BCWM1; chronic myeloid leukemia K562), as well as solid tumors (lung A549; pancreas BxPC3; glioma U87) compared to non-conditioned media.

In addition, conditioned media was derived from culturing 8 different types of cancer cells, including hematological malignancies and solid tumors were examined to determine if EPCs can migrate towards different types of tumors. A chemotaxis assay of EPCs migrating was performed towards media-derived from MM cell lines (MM.1S, H929, and OPM1), lymphoma cell line (BCWM1), and CML cell line (K562), which were cultured at $1\times10^6$ cells per 1 mL of RPMI1640 media for 24 hours, as well as solid tumors including lung (A549), pancreas (BxPC3) and glioma (U87) cell lines, which were cultured at $0.1\times10^6$ cells per 1 mL of DMEM media for 24 hours. The migrated HUVECs were counted in the lower Boyden chamber by flow cytometry after 24 hours. FIG. 4 demonstrates that EPCs migrated to media derived from hematologic malignancies as well as from solid tumors.

Lastly, the migration of EPCs to hematologic tumors such as multiple myeloma—MM.1S (FIG. 3A), as well as to solid tumors such as lung cancer—A549 (FIG. 3B), in a tumor-size-dependent manner. The same number of EPCs were applied to the upper compartment, while increasing numbers of MM cells were plated in the lower compartment of the chamber (0.02, 0.1, 0.2, 1 and $5\times10^6$ MM.1S-GFP+ cells per 1 mL of serum-free media RPMI1640). The EPCs were left to migrate towards MM cells for 24 hours, which were then counted in the lower chamber using flow cytometry. The number of EPCs migrated to media depends on cancer cell number and that homing of EPCs to MM in vitro was in a direct linear correlation with the number of MM cells ($R2=0.96$), which signifies that the EPCs chemotaxis is dependent on tumor size. These results demonstrated that EPCs migration in vitro directly correlates with tumor burden.

Example 2: Tumor Homing of EPCs In Vivo and Priming of EPCs

Besides sprouting from the pre-existing endothelium in the tumor, cancer cells utilize the recruitment of endothelial progenitor cells (EPCs) to build new blood vessels in the tumor vascular bed. EPCs are a subtype of stem cells with high proliferative potential which are capable of differentiating into mature endothelial cells thus contributing to neo-angiogenesis. In this process, EPCs respond to chemokine gradients that are formed in tumor tissues, which attract EPCs to home to tumors facilitating neo-angiogenesis. Previous work found EPCs play a crucial role in MM progression and that EPCs homing is CXCR7-dependent. In addition, EPCs home specifically to the tumors in MM (and other cancers), but not to normal tissues, and that migration of EPCs was depending on CXCL11 (CXCR7 ligand). Therefore, the goal of this study was to examine the tumor homing ability of EPCs in vivo and the ability to "prime" EPCs to migrate towards tumors.

Methods

Mouse Models of EPC Tumor Homing

Mice are be injected with indicated cancer cell lines, one cell line for each disease. 3 weeks after cell injection, EPCs are isolated from the BM and blood of 5 out of 10 mice, and labeled with different fluorescent labels. EPCs are then pooled, primed and injected to the remaining 5 mice. 24 hrs after EPCs injection, mice are sacrificed and their organs (Tumor, blood, liver, kidney, lung, muscle, brain and spleen) will be extracted. Distribution of EPCs in different organs are analyzed by flow cytometry.

Priming of EPCs

Figure 7A:
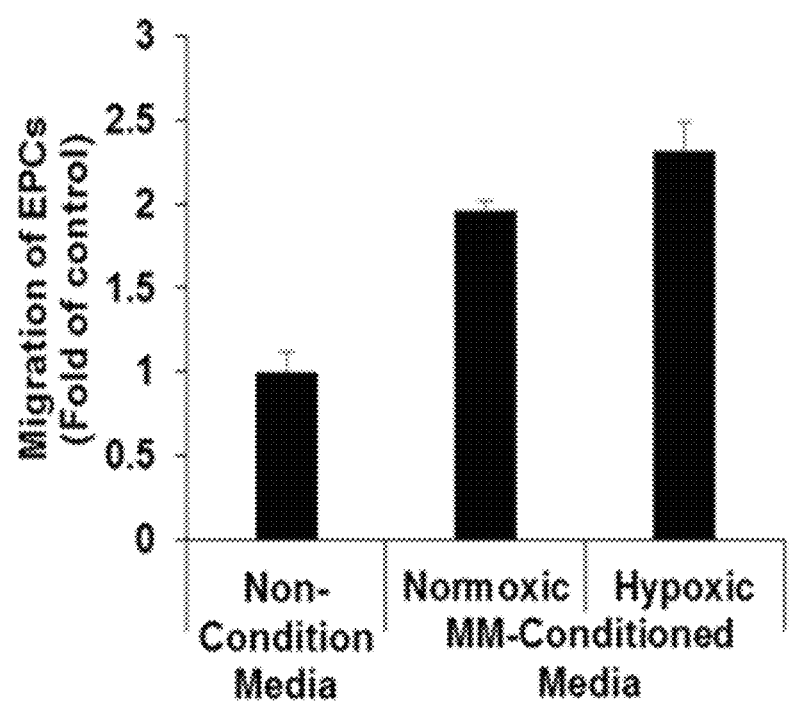
FIG. 7A-B include graphs showing "priming" of EPCs results in increased EPC homing to tumors.

Using Boyden chamber a chemotaxis assay in vitro was performed using Non-primed HUVECs (treated with non-conditioned RPMI media), or primed (treated for 2 hours with conditioned media from MM1S cells-GFP+ which were cultured in normoxia or in hypoxia for 24 hours) (FIG. 7A). Cells were then left to migrate towards MM-conditioned media for 24 hours. Cells that migrated to the lower chamber were counted using flow cytometry.

Non-primed HUVECs (treated with non-conditioned RPMI media), or primed (treated for 2 hours with conditioned media from MM1S cells-GFP+ which were cultured in normoxia or in hypoxia for 24 hours) were labeled with DiD and injected iv to MM-bearing mice in their bone marrow. After 24 hours, the bone marrow of the mice was extracted and the number of EPCs that homed to the tumor-containing bone marrow was analyzed by flow cytometry by detecting the number DiD-labeled EPCs (FIG. 5).

Results (ii) EPCs Preferentially Home to the Hematological Malignancy (Such as Multiple Myeloma-MM) and to Solid Tumors In Vivo To test homing of EPCs in tumor-bearing mice, local and disseminated, early in the tumor development and at advanced stages. Multiple tumor mouse models in vivo are utilized, including sub-cutaneous pancreatic cancer model by injecting BxPC3 pancreatic cancer cell line under the skin of nude mice (FIG. 5A); orthotopic glioma model by injecting GL261 glioma cells intracranially into the C57BL/6J mice (FIG. 5B); metastatic lung cancer model by injecting Lewis lung cancer (LLC) cells intravenously (IV) to C57BL/6J mice which results in developing lung nodules as well as liver metastasis (FIG. 5C); orthotopic localized breast cancer model by implanting B01-GFP+ breast cancer cells into the mammary fat pad of C57BL/6J mice, which shows restricted tumor growth in the mammary fat pad within the first 3 days post-implantation (FIG. 5D). In addition, mice 14 days post B01 cells implantation were used, which resulted in a metastatic breast cancer model detected as B01-GFP+ cell in multiple distant organs (FIG. 5E). Then, DiD-labeled EPCs were injected (CD34+, CD31+ endothelial cells purchased from AngioProteomie) IV into these mice ($10^6$ EPCs/mouse), and 24 hours after injection, mice were sacrificed, their organs harvested, digested, and the prevalence of the EPCs (and in some cases GFP+ cancer cells) in different organs was determined by flow cytometry. It was found that the homing of EPCs were restricted to localized tumors, with low numbers of EPCs detected in normal tissues including filtrating organs such as liver, spleen, lung and kidney (FIG. 5A-5D). These results provide a paradigm-shifting idea in drug delivery field, since the entrapment of drug delivery systems in the filtrating organs has been an unresolved problem for all injectable drug delivery systems up-to-date (81).

Figure 5A:
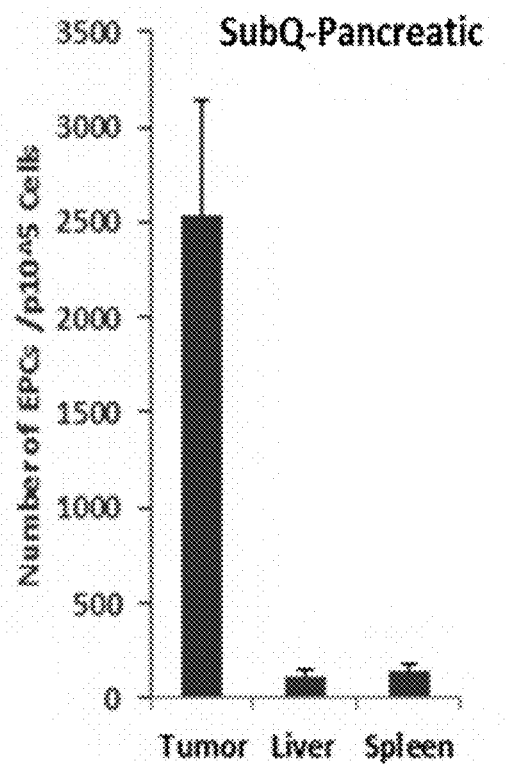
FIG. 5A-E include graphs showing EPCs home to a variety of different tumors in vivo.
Figure 5B:
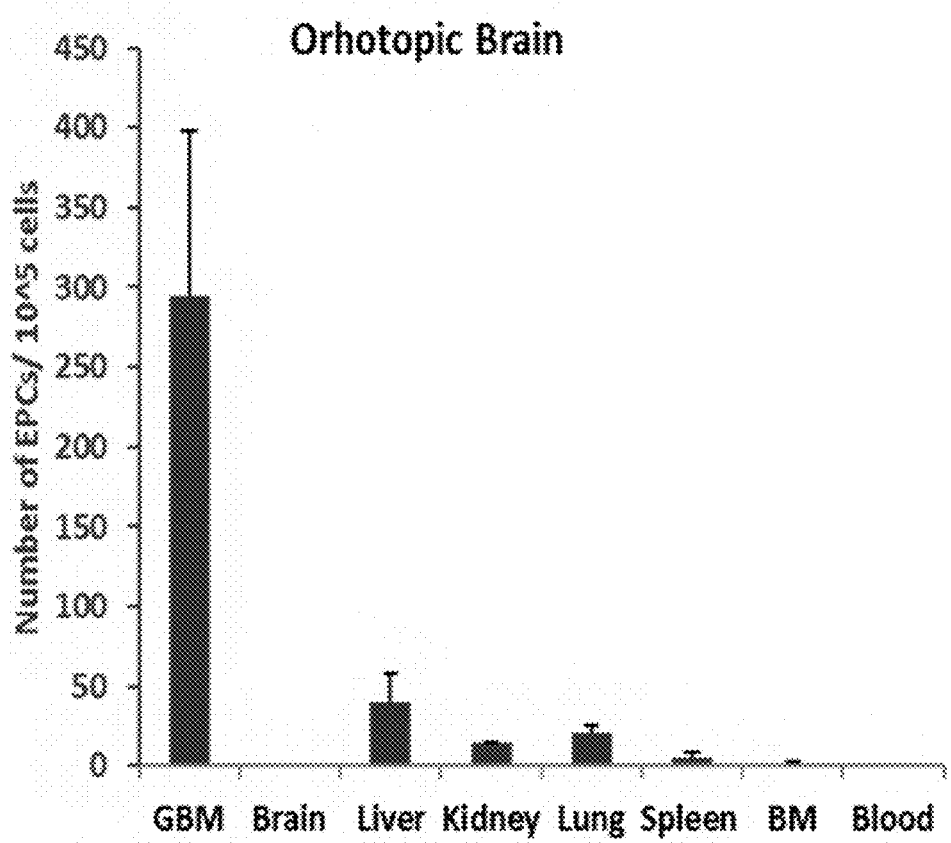
Figure 5C:
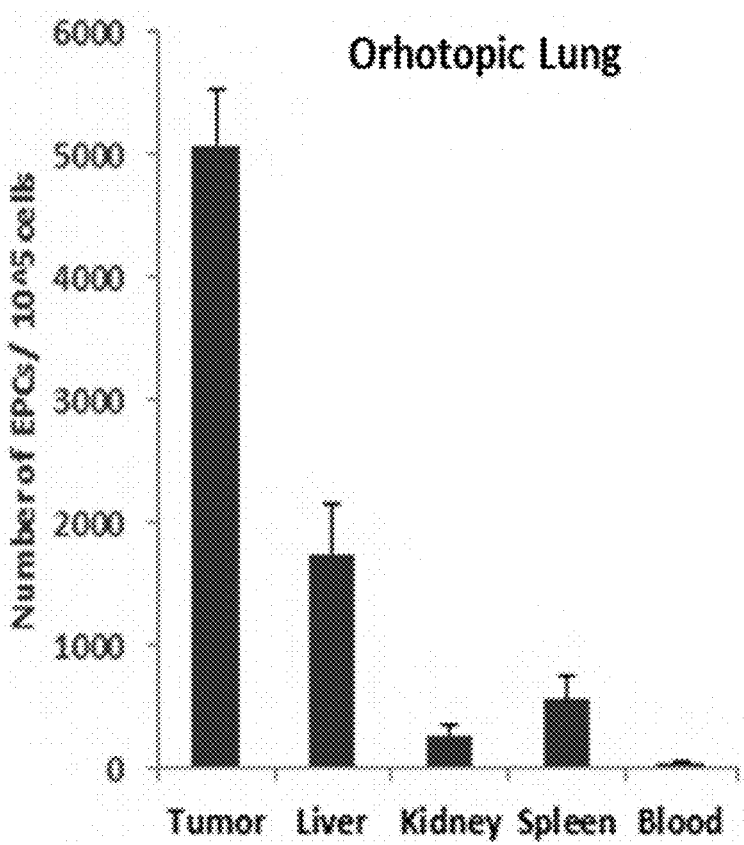
Figure 5D:
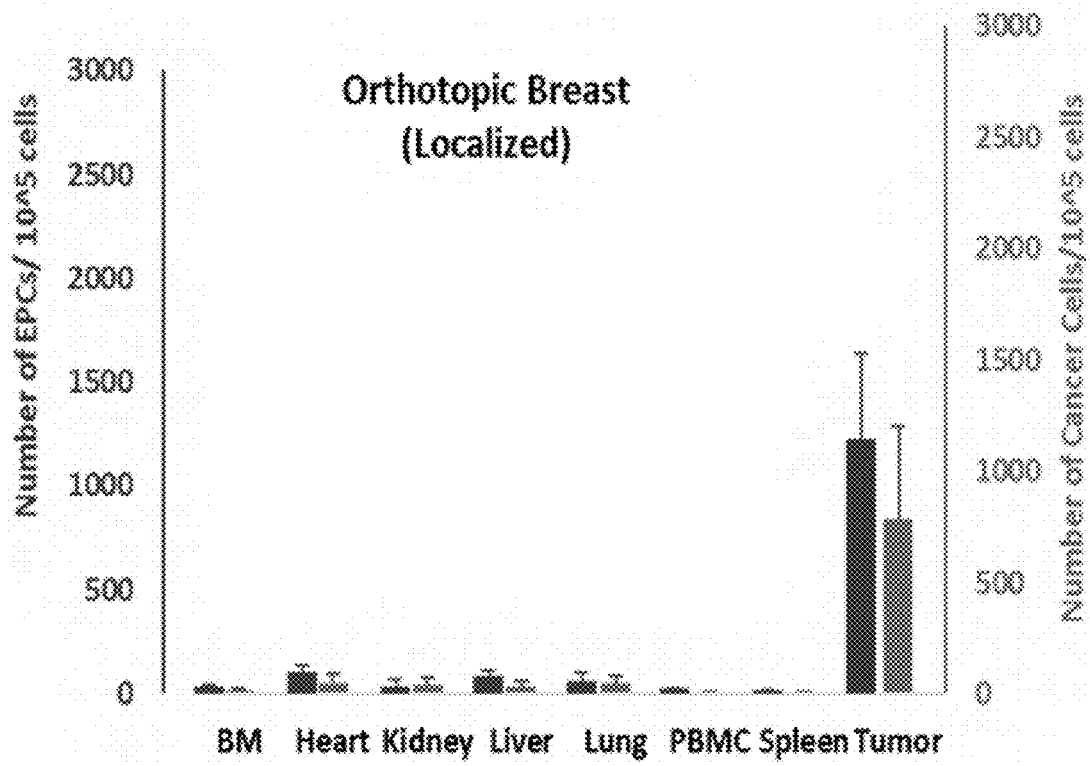
Figure 5E:
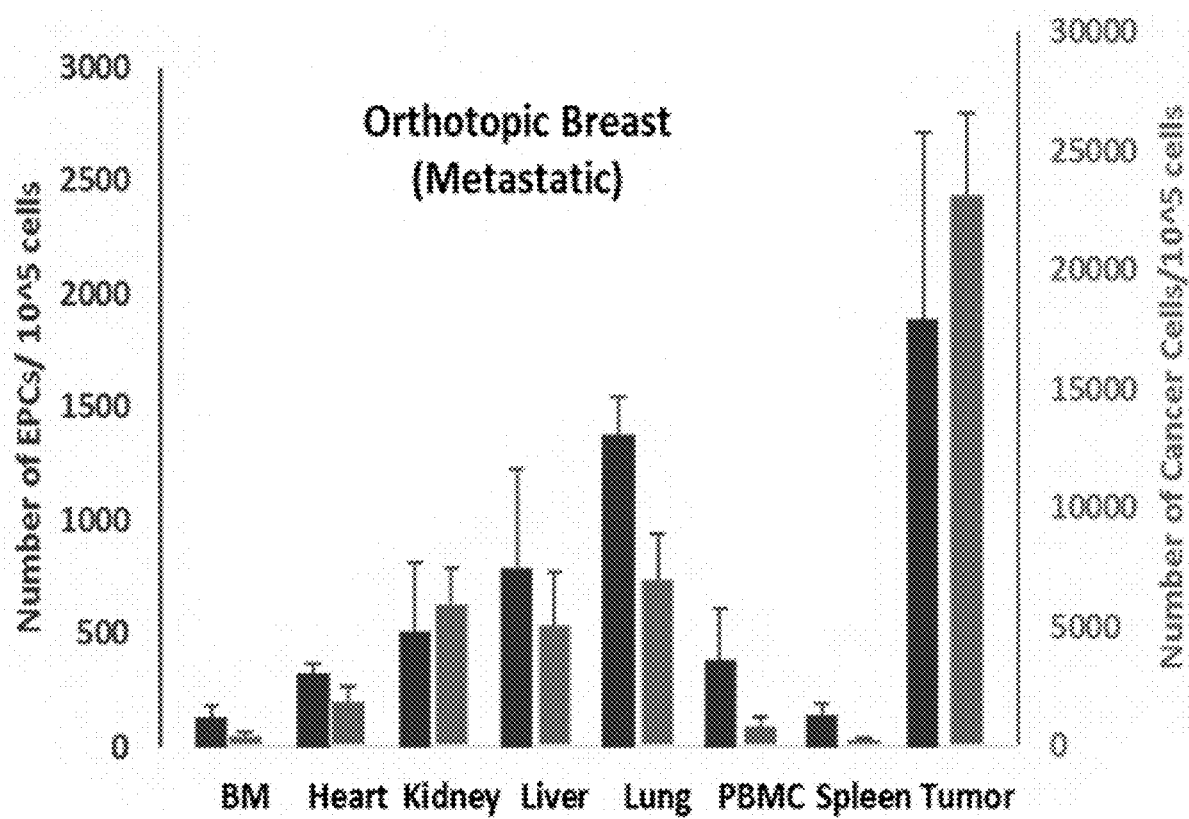

Another important finding is that EPCs crossed the blood-brain barrier (BBB) and homed to glioma tumors in the brain, while completely avoiding the normal part of brain in the same mouse (FIG. 5B). These results demonstrate that EPCs can overcome another classic problem in drug delivery which is crossing the BBB, which has been a challenge for different types of drug delivery systems/compounds/molecules (82). Moreover, it was found that even when the breast cancer model progressed into a metastatic disease, the EPCs homed to both the primary and the metastatic tumors in a fashion that "copied" the distribution and the size of the metastasis (FIG. 5E). These results emphasize the ability of EPCs to target and home to tumors regardless of the tumor size and location and that a specific tumor targeting using EPCs is a pan-cancer phenomena.

Figure 6A:
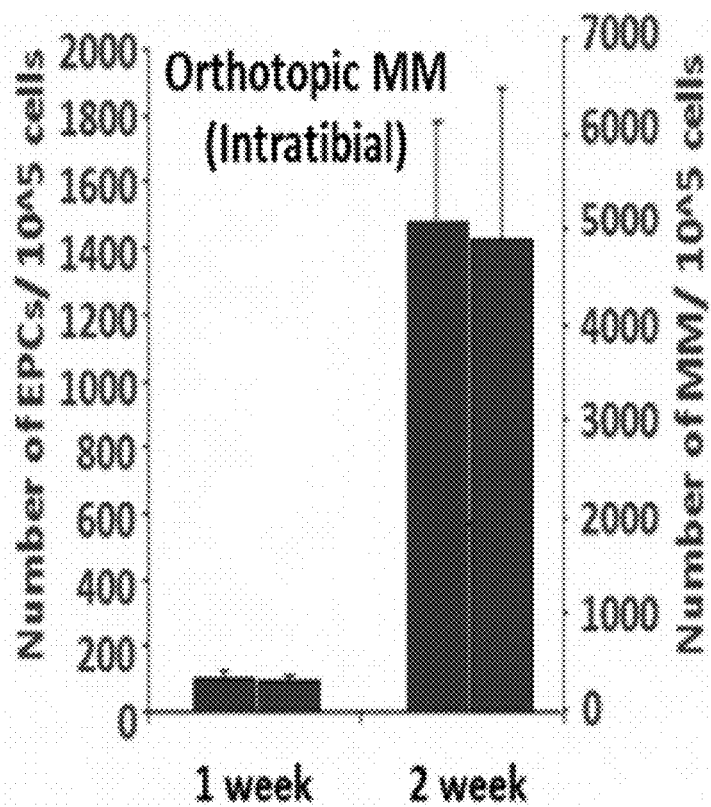
FIG. 6A-C include graphs showing homing of EPCs to localized or disseminated MM tumors.
Figure 6B:
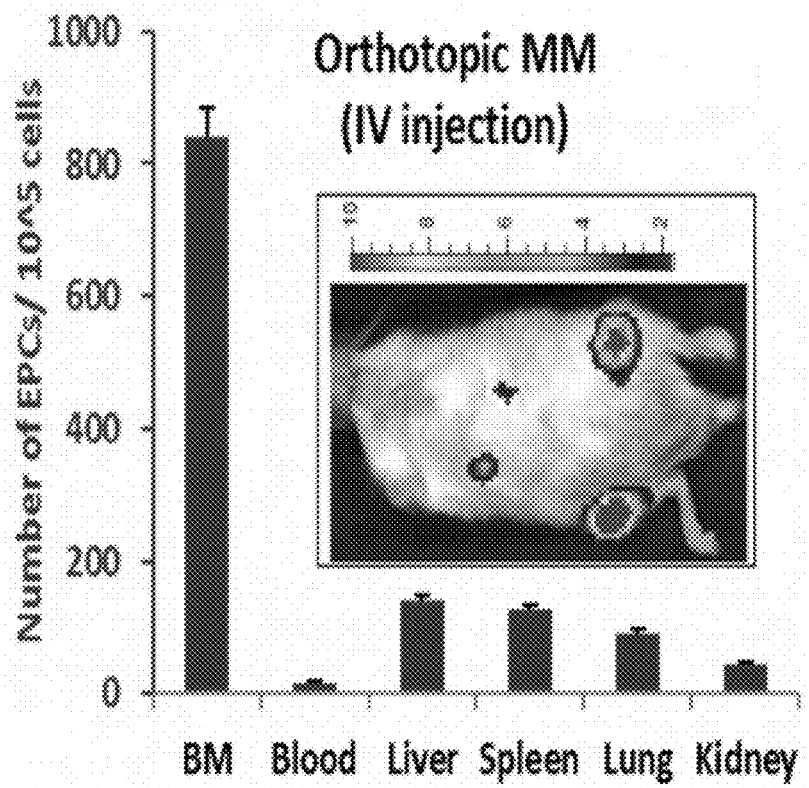
Figure 6C:
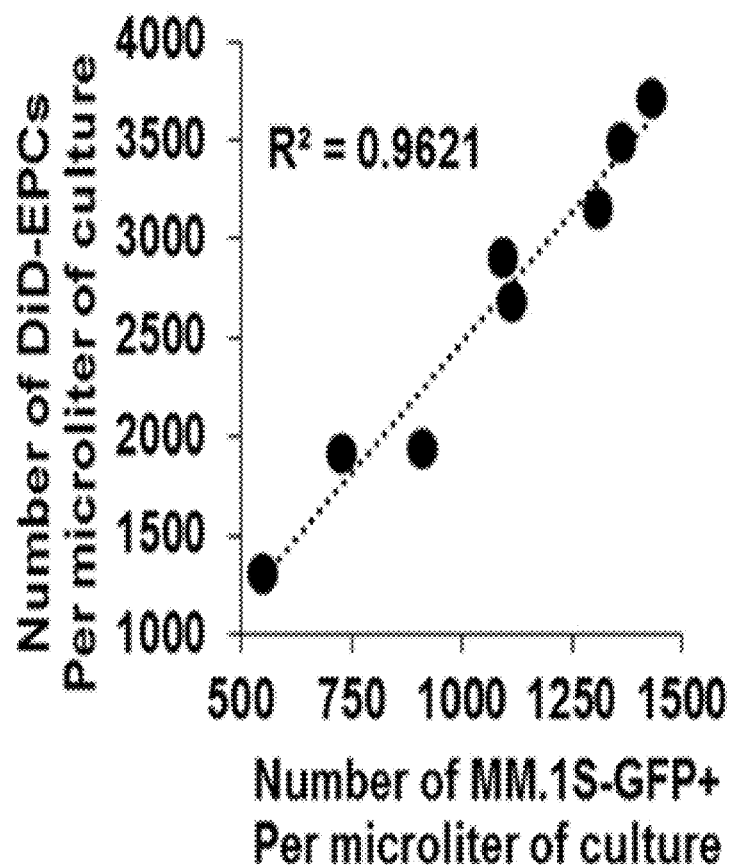

Subsequently, the specific homing of EPCs to localized or disseminated MM tumors was tested. For the localized orthotopic model, MM.1S-GFP-Luc+ cells were injected locally into the tibias of SCID mice and allowed them to grow for one or two weeks. Next, DiD-labeled EPCs were injected IV and 24 hours later the mice were sacrificed, tibias were collected; the BM was flushed with 1×PBS and analyzed for MM.1S and EPCs prevalence using flow cytometry. It was found that at one week post injection, the disease was small; while at two weeks post injection the disease was advanced (FIG. 6A). In a similar pattern, DiD-EPCs homed in low numbers to the tibia in week-1, and had significantly more homing in week-2 (FIG. 6A). To further demonstrate the specificity of EPCs homing to MM, a disseminated MM model was developed by injection of MM.1S-GFP-Luc+ cells IV, and after 4 weeks tumor development was confirmed by bioluminescence imaging (BLI), which found to be mainly in the BM in the femur, with low signal in the liver and spleen (FIG. 6B-Insert). Then, DiD-labeled EPCs were injected IV, and analyzed the biodistribution of the EPCs in different organs 24 hours post injection by flow cytometry. It was found that the homing of the EPCs to the myeloma BM was significantly higher than all the other organs, while still showing low homing to liver and spleen that showed lower tumor involvement (FIG. 6B), which suggests that EPCs preferentially home to the BM of the mice with active myeloma. Additionally, EPCs homed specifically to areas of MM tumor growth, with significantly higher number of EPCs in bigger tumors.

Further, GFP-labeled MM cells were injected injected intravenously to the mice and formed a disseminated for of the disease, but mainly localized in the bone marrow. Then, EPCs were labeled with DiD (a red-fluorescent dye) and injected through the tails vein, and the biodistribution of EPCs in the tumor-bearing mice was analyzed by extracting the different organs from the mice, and analyzing the presence of MM cells and EPCs in each organ by flow cytometry. This data shows that the EPCs homed mainly in the bone marrow (BM) where the highest tumor burden was detected. Significantly low presence of EPCs was detected in other normal organs which did not have MM. These results demonstrated that the EPCs home preferentially to tumors in vivo, in hematological malignancies (such as multiple myeloma).

Next, pancreatic cancer cells were injected subcutaneously to the mice to form a localized pancreatic cancer model, and lung cancer cells were injected intravenously to form a disseminated (mainly to liver) lung cancer model. Then, EPCs were labeled with DiD (a red-fluorescent dye) and injected through the tails vein, and the biodistribution of EPCs in the tumor-bearing mice was analyzed by extracting the different organs from the mice, and analyzing the presence of EPCs in each organ by flow cytometry. The EPCs homed mainly to the localized subcutaneous pancreatic models, and to the tumors in the lung as well as to the metastasis in the liver in the lung cancer model. Significantly low presence of EPCs was detected in other normal organs which did not have tumor. These results demonstrated that the EPCs home preferentially to tumors in vivo, in solid malignancies (such as pancreatic and lung cancers).

Angiogenesis is a process that happens in both primary and in metastatic tumor sites and as noted above, the administered EPCs also homed to organs that had metastasis. To confirm that this is the case, an orthotopic tumor model breast cancer was developed (by injecting GFP-labeled breast cancer cells in the fat pad) in which the tumors start as localized, then (after two weeks) the tumors metastasize to various distant organs, similar to what happens in the progression of breast cancer patients. EPCs were labeled with DiD (a red-fluorescent dye) and injected through the tails vein of mice at the localized stage and mice at the metastatic stage, and the biodistribution of the breast cancer cells and EPCs in the tumor-bearing mice was analyzed by extracting the different organs from the mice, and analyzing the presence of EPCs in each organ by flow cytometry. In the early stage, the tumor was localized in the fat pad, with no evidence for tumor in other organs, similarly, the EPCs homed specifically to primary tumor in the fat pad with no evidence for home in any other organs. It was also confirmed that in the later stage breast cancer cells metastasized to different organs including kidney, liver and lung. Further, it was found that the EPCs distribution followed, exactly, the distribution of the metastasis of the breast cancer cells in the different organs, in addition to high presence in the primary tumor site. These results demonstrated that the EPCs specifically home to the primary tumors, as well as follow the metastasis to the different other organs.

Glioma is one of the hardest cancer to treat due to the presence of the Blood Brain Barrier (BBB), which prevents therapy from penetrating to the brain for the treatment of Glioma. The BBB is a major hurdle, since until now there is not any clinically available technology to allow drug crossing through the BBB. In this study, glioma cells were implanted orthotopically into the mice brains to form a localized glioma cancer model. Then, EPCs were labeled with DiD (a red-fluorescent dye) and injected through the tails vein, and the biodistribution of EPCs in the tumor-bearing mice was analyzed by extracting the different organs from the mice, and analyzing the presence of EPCs in each organ by flow cytometry. It was found that the EPCs crossed the BBB and homed mainly to glioma (brain tumor) and not to the normal brain. Significantly low presence of EPCs was also detected in other normal organs which did not have tumor. These results demonstrated that the EPCs cross (BBB), home to the glioma tumors specifically, with no accumulation in the healthy part of the brain.

(iii) Priming EPCs Significantly Improves Tumor Homing

The next aspect which we investigated was "priming" EPCs with hypoxia- and cancer-conditioned media to improve EPCs homing. EPCs are mobilized from the BM to the circulation and home to tumor areas in response to chemokines and cytokines secreted by cancer cells to facilitate angiogenesis, especially in hypoxic tumors. Therefore, the effect of "priming" EPCs with hypoxia- and cancer-conditioned media was tested in connection with the homing of EPCs to MM tumors, both in vitro and in vivo. In vitro, MM cells were incubated in normoxia (21% $O_2$) or hypoxia (1% $O_2$) for 24 hours, and then EPCs were treated with conditioned media from normoxic or hypoxic MM cells for 1 hour and applied to the upper compartment of a Boyden chamber. It was found that priming the EPCs with MM-conditioned media improved the migration of EPCs (2-fold of non-conditioned); the priming with hypoxic MM media improved the migration in vitro modestly (FIG. 7A).

Figure 7B:
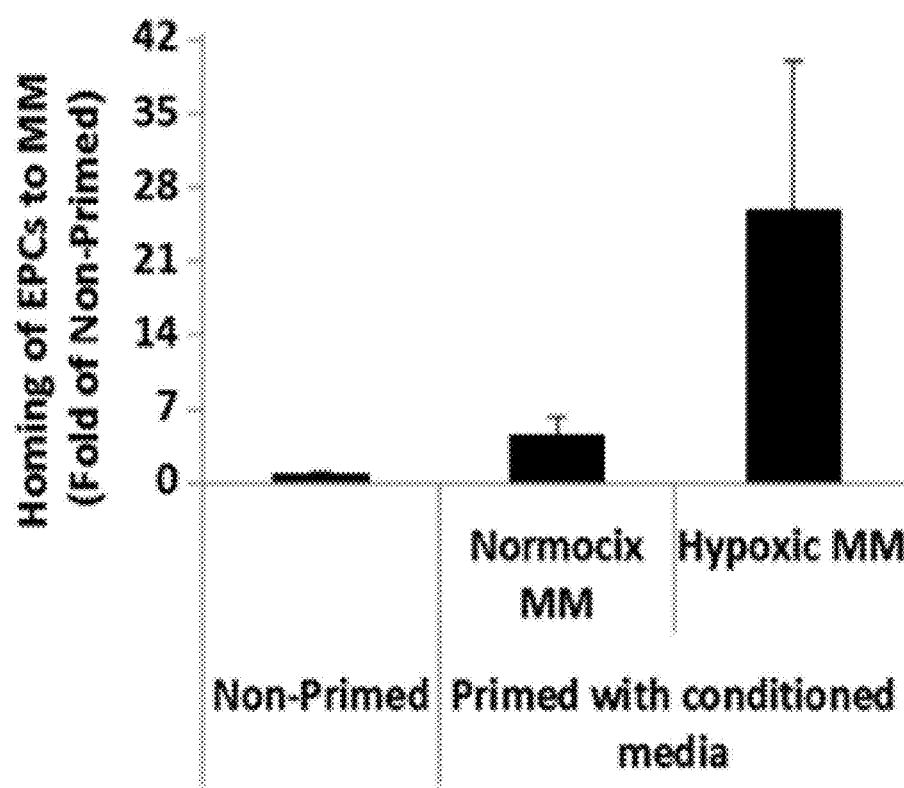

Based on the results above, it was tested whether exposing EPCs to normoxia or hypoxia will affect their homing in MM-bearing mice. In vivo, the effect was more significant; "priming" with conditioned media from normoxic MM cells improved the homing of EPCs about 7-fold, while media from hypoxic MM cells about 27-fold compared to non-primed EPCs (FIG. 7B).

Example 3: Engineered EPCs for Treatment and Imaging of Cancer

One of the main limiting factors of current treatments is side effects exerted on normal tissues. The emphasis in cancer treatment in general has shifted from cytotoxic, non-specific chemotherapies to molecularly targeted, rationally-designed therapies promising greater efficacy and fewer side effects. Cellular immunotherapy such as CAR-T cells is an emerging strategy in cancer. One of the common disadvantages of the current cellular immunotherapy approaches is the ability to only target a single epitope on the cancer cells, while it is evidently known that tumors consist of different clones of cancer cells expressing a landscape of heterotypic epitopes, which may cause these technologies to only affect some clones of the tumor and not others. As shown above, EPCs have the ability to home to all cancer types since angiogenesis is a pan-cancer mechanism. Therefore, the goal of this study was to examine the use of EPCs as a first-of-class for cellular theranostic which will have a pan-cancer targeting.

Methods

Loading EPCs with Anti-Cancer Agents (Bortezomib (BTZ), Titanocene (Tc), and 4-Borono-L-Phenylalanine (BPA))

Figure 8A:
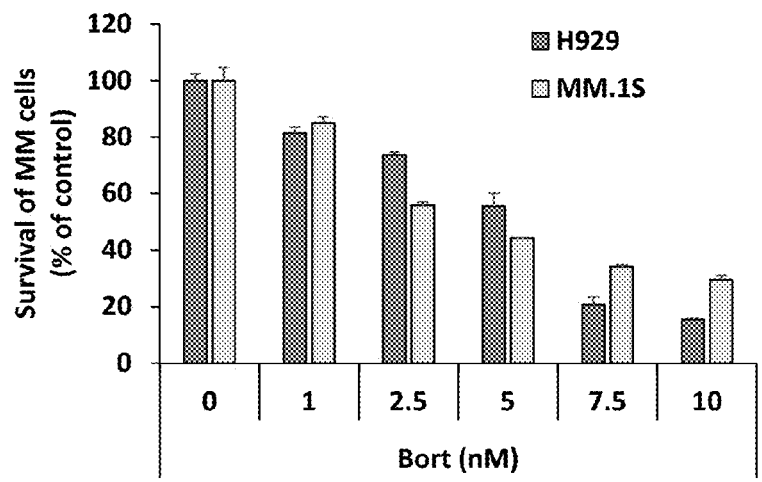
FIG. 8A-D include graphs depicting the viability and efficacy of loading EPCs with bortezomib.
Figure 8B:
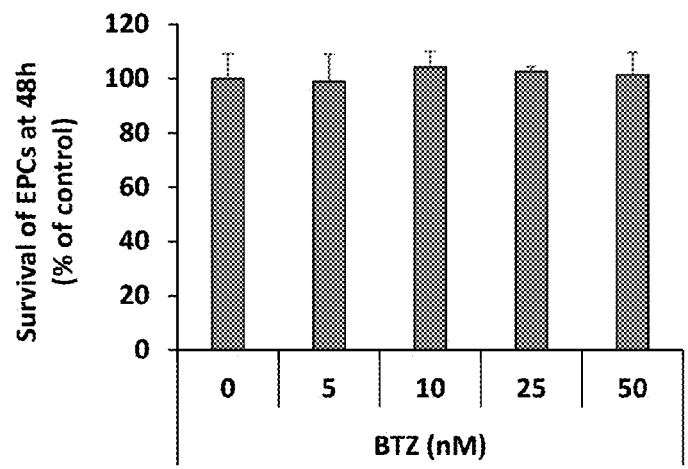
Figure 8C:
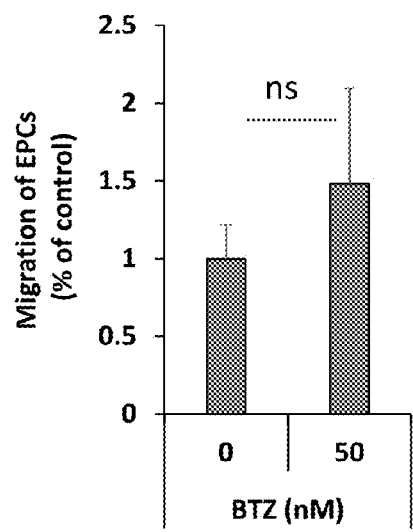

Anticancer agents have preferential cytotoxic effects on cancer cells compared to non-malignant cells (such as EPCs). Therefore we tested the effect of BTZ (anti-cancer drug) on the survival of malignant MM cells (MM1s and H929) and on EPCs, in which cells were treated with increasing concentrations of Bortezomib, and the killing effect was evaluated after 48 hours using MTT assay (FIGS. 8A and B). Also EPCs were treated with and without high-dose of BTZ (50 nM) and we measured the in vitro migration of the EPCs towards MM-conditioned media, using a Boyden chamber migration assay, and the number of migrating EPCs was analyzed by flow cytometry (FIG. 8C).

Figure 8D:
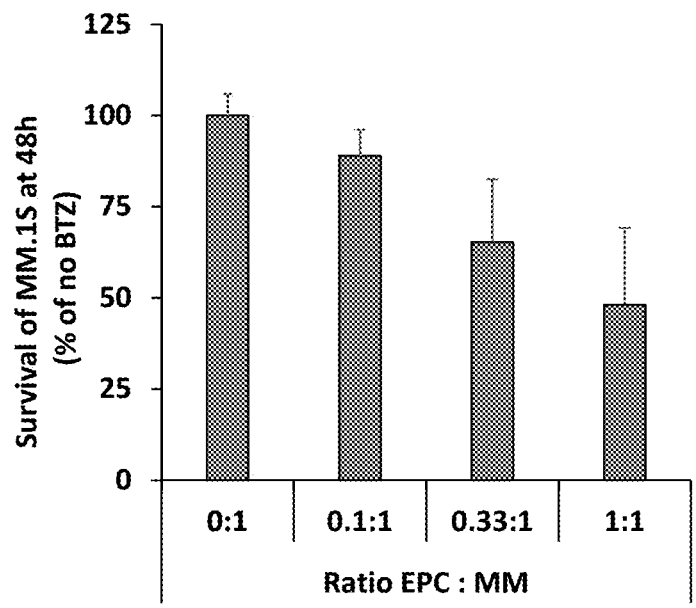

Furthermore, to mimic the cytotoxic effect of BTZ loaded EPCs on MM cells, EPCs were treated with high-dose BTZ (50 nM), washed from drug that was not uptaken. Increasing numbers of BTZ-loaded EPCs were co-cultured with MM cells (same number) for 48 hours, and the number of surviving MM cells in the culture was analyzed by flow cytometry (FIG. 8D)

Figure 9A:
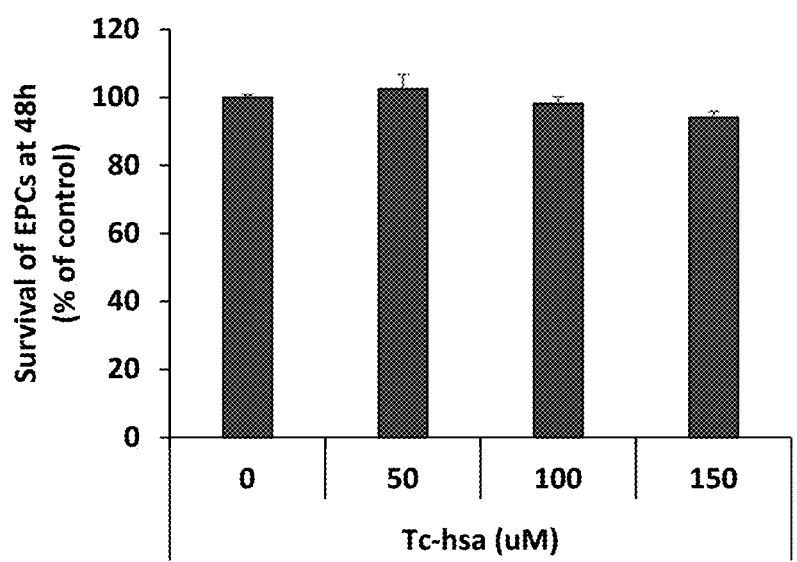
FIG. 9A-D include graphs depicting the viability and efficacy of loading EPCs with titanocene.
Figure 9B:
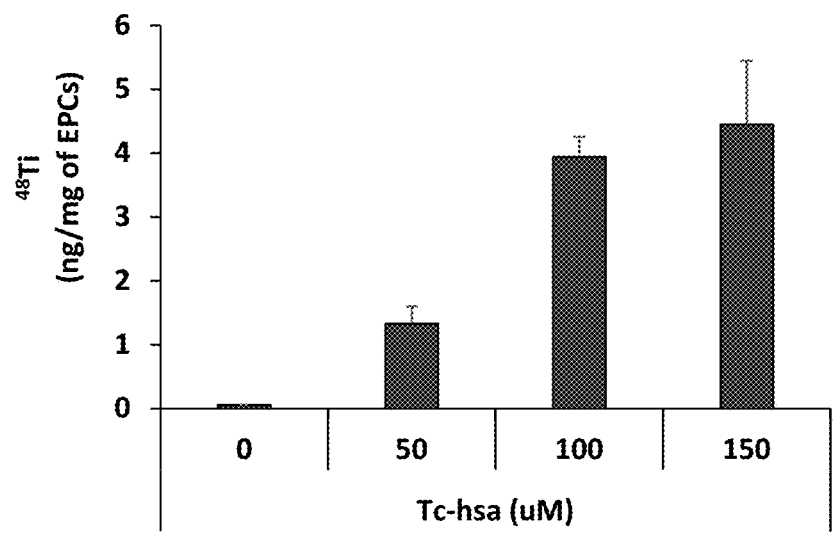
Figure 9C:
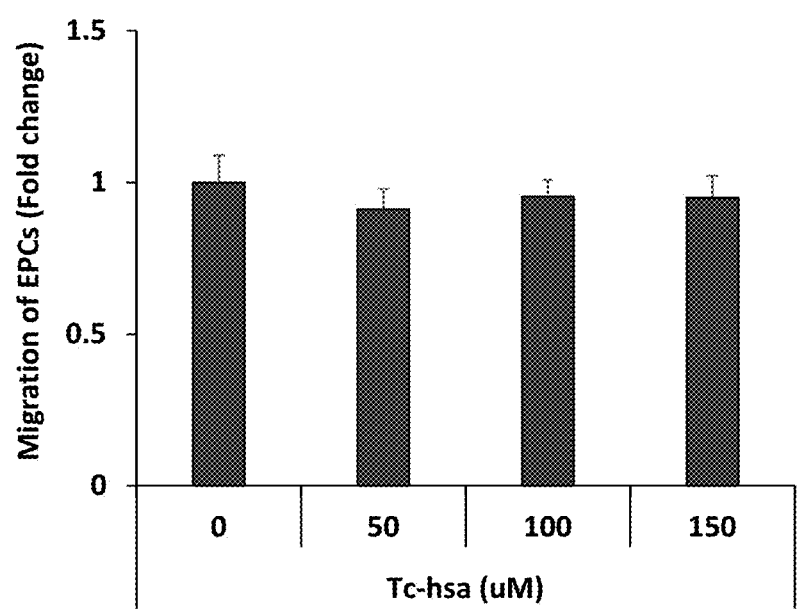
Figure 10A:
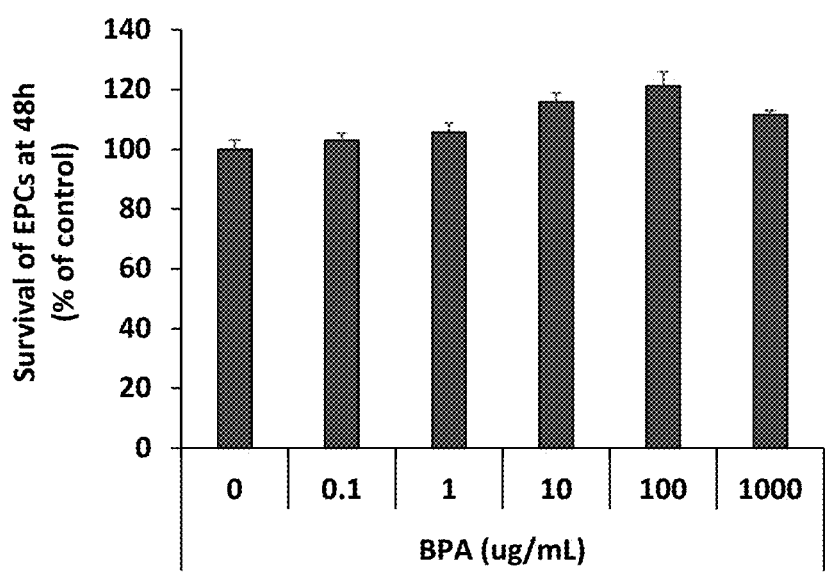
FIG. 10A-D include graphs depicting the viability and efficacy of loading EPCs with 4-borono-L-phenylalanine for Boron Neutron Capture Therapy.
Figure 10B:
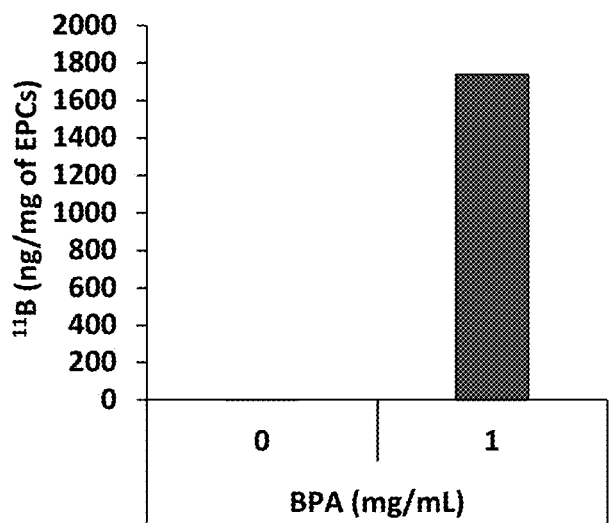
Figure 10C:
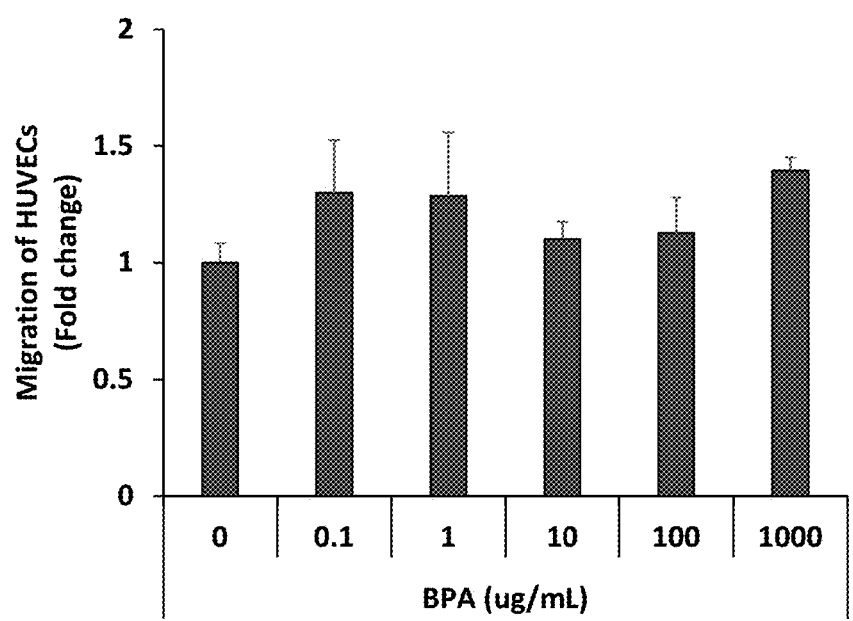

Prodrugs such as TC and BPA are inert agents that are not supposed to have effect by them selves on cancer or normal cell survival, but when activated using positron emission and neutrons, respectively, these agents become active drugs and kill the cell that they reside in and adjacent cells next to it. We tested the effect of TC and BPA (prodrugs) on the survival of EPCs, in which cells were treated with increasing concentrations of these, and the killing effect was evaluated after 48 hours using MTT assay (FIGS. 9A and 10A). And to confirm the loading of EPCs with TC and BPA, we treated the EPCs with increasing doses of TC and BPA, digested the cells with nitric acid, and used ICP-MS to detect the level of Titanium and boron in the EPCs, respectively (FIGS. 9B and 10B). Also EPCs were treated with and without increasing doses of TC and BPA and we measured the in vitro migration of the EPCs towards MM-conditioned media, using a Boyden chamber migration assay, and the number of migrating EPCs was analyzed by flow cytometry (FIGS. 9C and 10C).

Figure 9D:
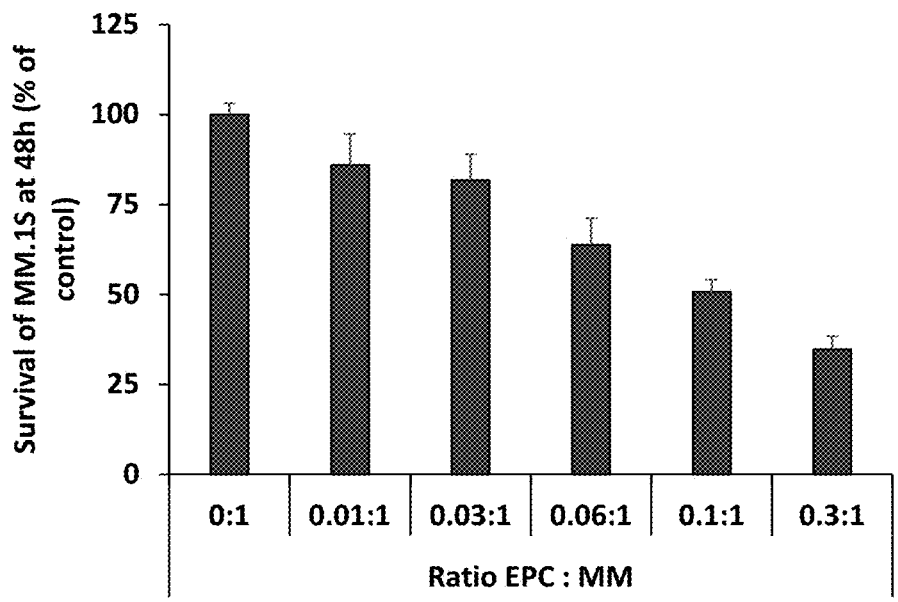

Furthermore, to mimic the cytotoxic effect of TC and BPA, we loaded EPCs with TC and BPA, and increasing numbers of TC or BPA-loaded EPCs were co-cultured with MM cells (same number) for 48 hours. In the case of TC, the coculture was treated with the positron emitter 18F-FDG to activate the TC and the number of surviving MM cells in the culture was analyzed by flow cytometry (FIG. 9D). Moreover, for the co-culture with BPA-loaded EPCs we analyzed the boron content of the whole culture using ICP-MS, it is acceptable in the field that any level of boron above 20 ng boron/mg tissue is enough for successful therapy.

Labeling EPCs with Imaging Agents (LS-542, $^{18}$F-FDG, $^{89}$Zr, and $^{64}$Gd)

Imaging agents such as LS-542 (florescence imaging), 18F-FDG (PET imaging), 89-Zr (PET imaging), and 64Gd (MRI imaging) are widely used for cancer imaging.

Figures 10D, 11A:
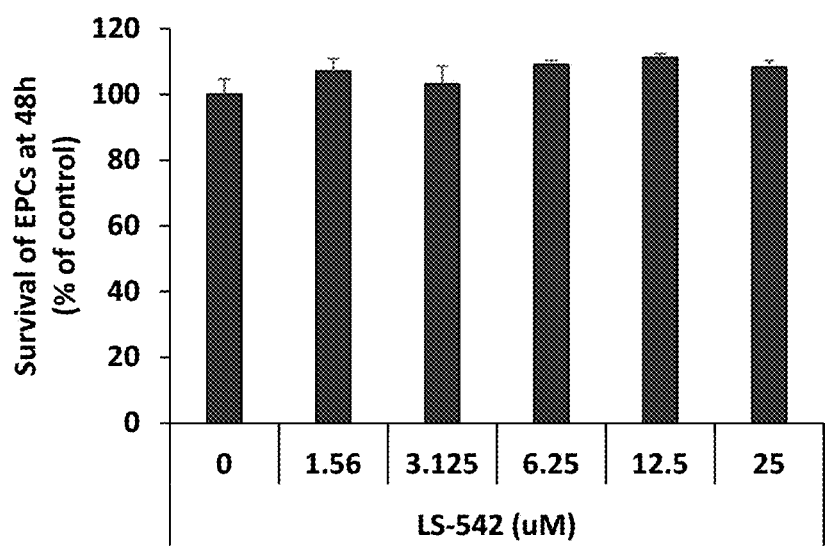
FIG. 11A-D include graphs depicting the viability and efficacy of loading EPCs with LS-542 for NIR imaging.
Figure 11B:
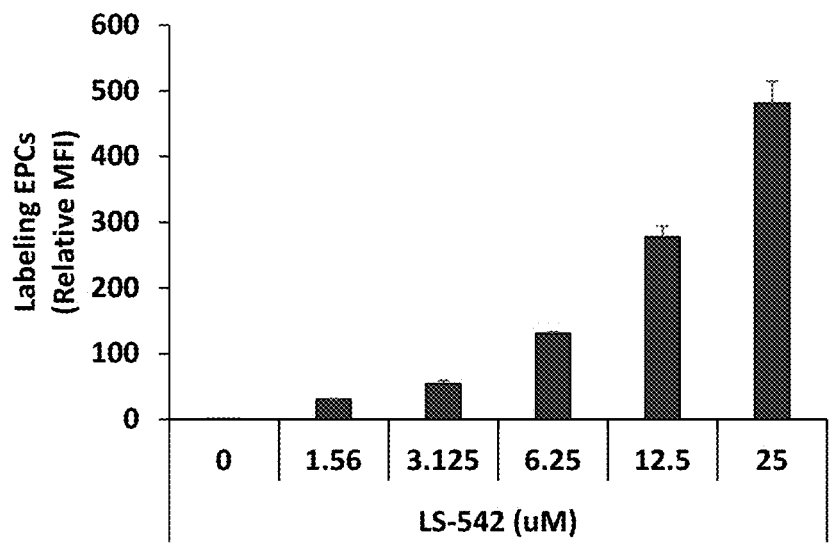

These agents have no cytotoxicity effect, to confirm that we tested the effect of LS-542, (as a model of an imaging agent) on survival of EPCs, in which cells were treated with increasing concentrations of these, and the killing effect was evaluated after 48 hours using MTT assay (FIG. 11A). And to confirm the loading of EPCs with LS-542, we treated the EPCs with increasing doses of LS-542, and the amount of labeling was measure by the mean-flurescence intensity of the dye by flow cytometry (FIG. 11B). Also EPCs were treated with and without increasing doses of LS-542 and we measured the in vitro migration of the EPCs towards MM-conditioned media, using a Boyden chamber migration assay, and the number of migrating EPCs was analyzed by flow cytometry (FIG. 11C).

Figure 11C:
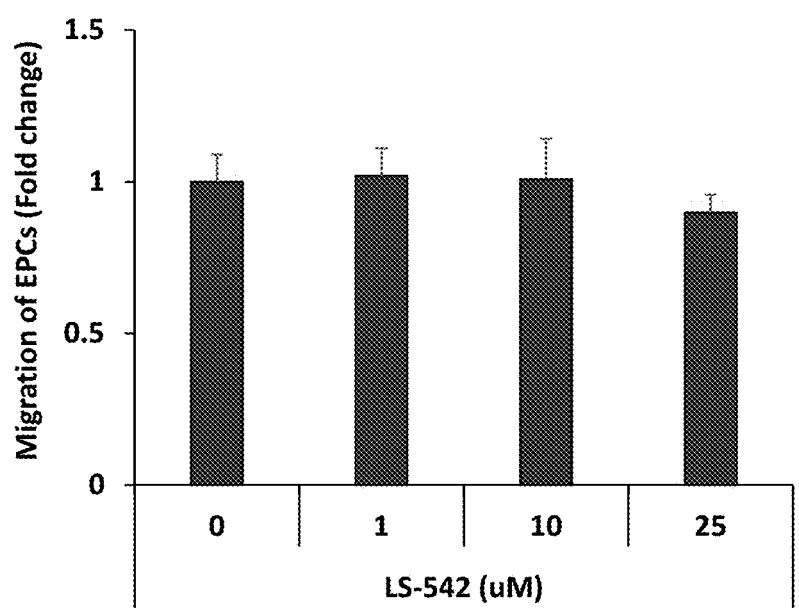

Furthermore, we injected the LS-542-loaded EPCs to MM-bearing mice (Sub-Q on the lower back) via tail vein, and the accumulation of the EPCs in the tumor was detected by NIR-camera before injection, 30 minutes after injection, and 24 hours after injection (FIG. 11C).

Figure 12A:
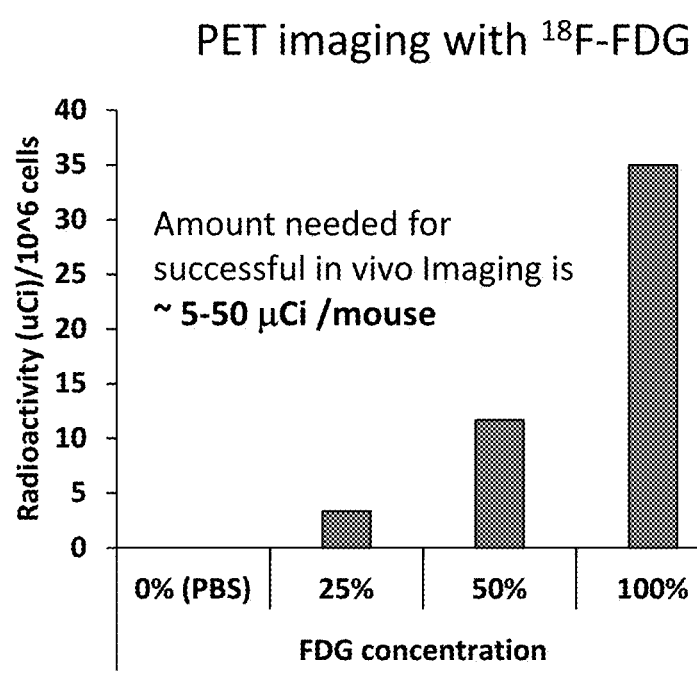
FIG. 12A-C include graphs depicting EPCs can be loaded with other imaging agents for a variety of imaging applications such as PET and MRI.
Figure 12B:
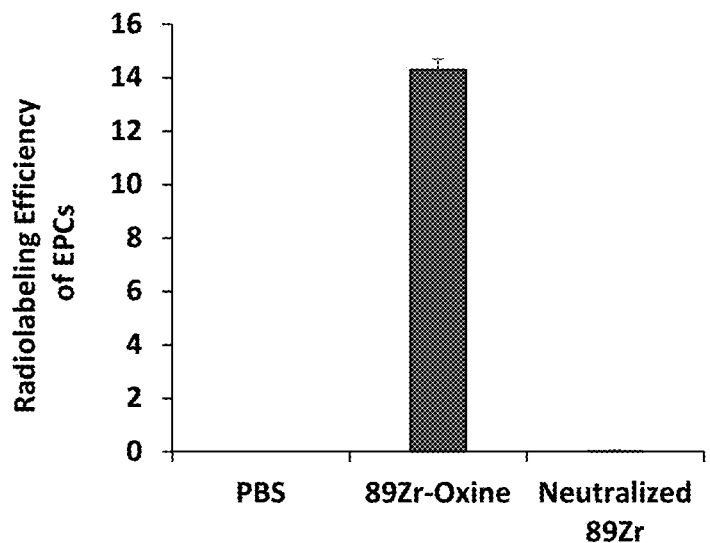
Figure 12C:
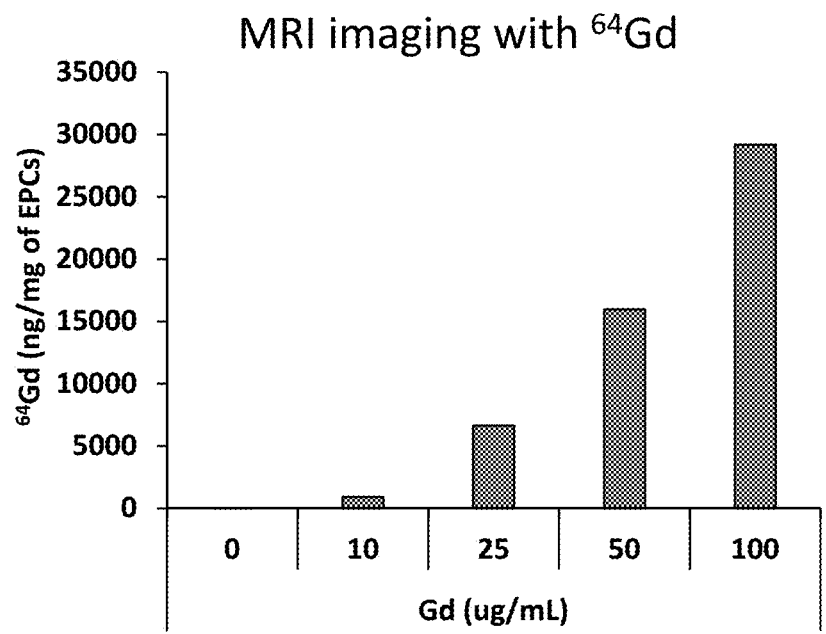
Figure 13:
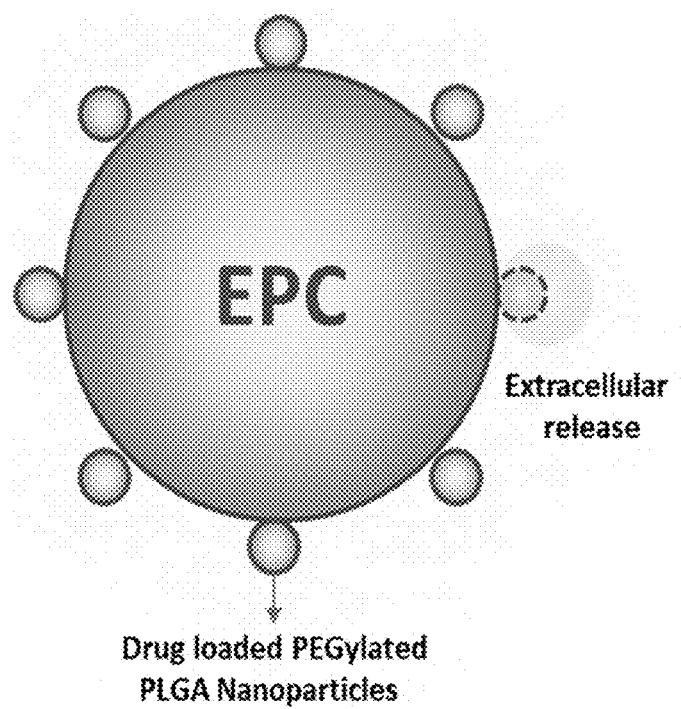
FIG. 13 is a schematic showing the loading of the EPCs to surface binding of PEGylated-PLGA nanoparticles-loaded with conventional drugs (such as bortezomib).

Furthermore, we demonstrated that EPCs can be loaded with other imaging agents efficiently. And to confirm this, we treated the EPCs with increasing doses of 18F-FDG (PET imaging), 89-Zr (PET imaging), and 64Gd (MRI imaging), and the amount of labeling was measure by radiation counter for FDG and Zr (FIGS. 12A and D); and by digesting the cells and analyzing the amount of Gd by ICP-MS (FIG. 12C).

Results (iv) EPCs with Anti-Cancer Drug Such as Bortezomib (BTZ)

EPCs has different sensitivity to chemotherapy and radiotherapy than cancer cells (much less sensitive since they are not proliferating as fast), therefore, loading (treat with high dose for short time) EPCs with chemotherapies or radiotherapies and make them carry it to the tumors, to kill the tumors. While BTZ kills myeloma cells at low concentration ($IC_{50}$ of 5 nM) (FIG. 8A); EPCs are not sensitive to BTZ up to 50 nM (FIG. 8B). Therefore, EPCs were loaded with BTZ (50 nM for 2 hrs), and confirmed that this did not affect the migration of EPCs towards cancer cells (FIG. 8C). But, when loaded with BTZ, and co-cultured with MM cells in vitro, BTZ-loaded-EPCs killed MM cells in a dose-dependent manner (FIG. 8D). These results demonstrated that the EPCs loaded with anti-cancer drug such as BTZ does not affect EPCs survival and functional properties (chemotaxis to tumor), and BTZ-loaded EPCs efficiently induce cancer death.

(v) EPCs Loaded with Photodynamic Pro-Drug Such as Titanocene.

EPCs can be loaded with prodrugs which can be activated after arriving to the tumor site, but has no effect on the EPCs. On example photodynamic therapy, where and inert drug is delivered to the tumor and it is activated with light or radiation to release cytotoxic derivatives such as reactive oxygen species and kill the tumors. In this study Titanocene as a prodrug was used and loaded into EPCs, and it had no effect on the survival (FIG. 9A) or migration of EPCs to tumor (FIG. 9C). It was further confirmed that EPCs where actually loaded with Titanocene by detecting the presence of Titanium in the EPCs using inductively coupled plasma mass spectrometry (ICP-MS) (FIG. 9B). Then EPCs were loaded with Titanocene and co-cultured with MM tumor cells and Titanocene was activated using the position emission, which caused killing of MM cells in a dose-dependent manner (FIG. 9D). These results demonstrated that the EPCs loaded with inert prodrugs that has no cytotoxic effect on EPCs, such as Titanocene, which can be activated (with light or radiation) after the EPCs home to the tumors, and as a result kill the tumors.

To further explore EPCs as a "Trojan horse" drug delivery carrier, we loaded them with increasing doses of Titanocene (Tc), a compound known for therapeutic efficacy when activated with Cerenkov radiation. The effect of Tc on the cell vitality/viability by staining the cells with viability dye (calcein-UV) and propidium iodide (PI) and analyzing by flow cytometry was tested. To ensure that the staining does not change the biological properties, the effect of Tc on the EPCs functionality based on migration of EPCs towards MM cells using Boyden chamber was tested. It was found that Tc was not toxic to EPCs up to 150 μM; similarly, the same concentration range did not affect the migration of EPCs to conditioned MM media, in vitro. Next, the intracellular Titanium (48Ti) content in the EPCs using Inductively Coupled Plasma-Optical Emission Spectrometer (ICP-MS) was measured, after treatment with the nontoxic concentration range of Tc. It was found that the cellular content of Titanium was correlated with the concentration in the solution, reaching 5 ng Titanium/mg EPC's. These results emphasize the feasibility of loading EPCs with a therapeutic moiety without changing their viability or homing properties. The ability of the Tc-loaded EPC's to induce cell toxicity in MM cells when activated with Cerenkov radiation using 18F-FDG was further tested. MM.1S-GFP+ cells were treated with increasing numbers of Tc-loaded EPCs which were activated by addition of 100 μCi $^{18}$F-FDG to the culture and analyzed the MM survival by absolute count of the MM-GFP+ cells using flow cytometry. It was found that the Tc-loaded EPCs, when activated by $^{18}$F-FDG, induced a dose-dependent killing of MM cells in vitro. These results demonstrate the feasibility of treating/killing MM cells with Tc-loaded EPCs. It is important to note that the ratio between the EPC/MM in the culture was very low 1-6 EPCs/100 MM cells; while in comparison with other cellular therapies, such as CAR-T cells, require 3-10 CAR-T/1 MM cells, which emphasized the efficacy of EPCs as a novel cellular therapy.

(vi) EPCs Loaded with Boron Such as 4-Brono-L-Phenylalanine (BPA) for Boron Neutron Capture Therapy (BNCT).

Another example in which EPCs can also be loaded with prodrugs which can be activated after arriving to the tumor site, but has no effect on the EPCs is loading with Boron-containing compounds for Boron Neutron Capture Therapy (BNCT). In this therapy, when irradiated with neutrons, boron atoms capture the neutron and undergo nuclear fission to become Lithium and Helium and release a high dose of energy that kills the cells where the boron atoms are uptaken. Neither the boron compounds nor the neutrons are cytotoxic, but when combined they induce massive killing of cells. For BNCT to be successful, a cancer tissue should include at least 20 ng boron/mg of tissue.

In this study 4-Borono-L-phenylalanine (BPA) as a prodrug was used and loaded into EPCs. It was found that BPA had no effect on the survival (FIG. 10A) or migration of EPCs to tumor (FIG. 10B). Further it was confirmed that EPCs where actually loaded with boron by detecting its presence in the EPCs using inductively coupled plasma mass spectrometry (ICP-MS) (FIG. 10C). Then EPCs were co-cultured with cancer cells at different ratios and detected if the boron content of the entire culture was meeting the threshold for BNCT, and it was found that any ration above 2.5% of EPCs was enough to meet the threshold for successful BNCT, in the higher cases of 1:1 ratio, the amount of boron detected was about 40-fold higher than the amount needed for BNCT (D). These results demonstrated that the EPCs can be loaded with boron as an inert prodrug that has no cytotoxic effect on EPCs, which can then be activated with neutrons for BNCT.

(vii) EPCs Labeled with LS-542 for NIR Imaging.

Figure 11D:
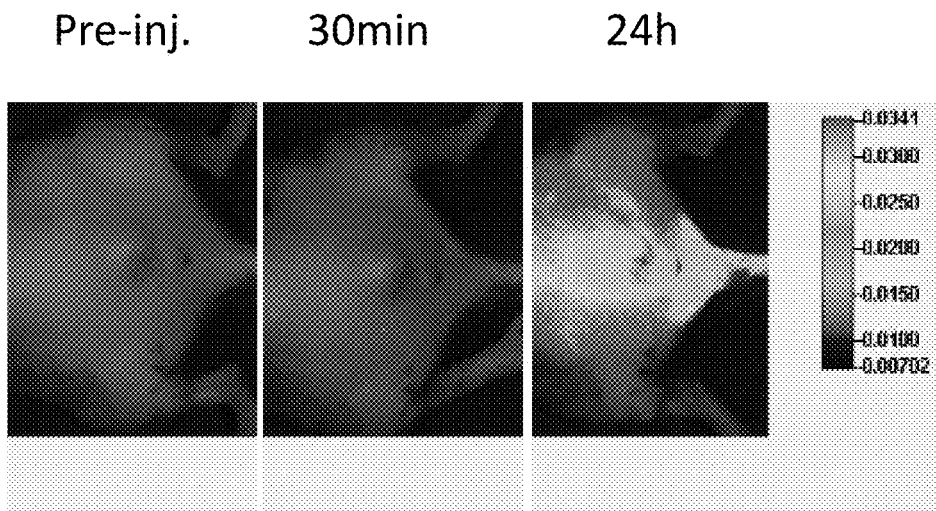

The specific homing of EPCs to tumor can be also used for imaging of primary and metastatic tumors. A common imaging technology is near-infra-red imaging, therefore, EPCs were loaded with LS-542 (a NIR-dye), and demonstrated that the dye does not cause any cytotoxic effects (FIG. 11A) or change the migration of EPCs to tumor (FIG. 11B). Furthermore, it was confirmed that the labeling efficiency of EPCs with LS-542 was directly proportional with the concentration based on relative mean fluorescent intensity (RMFI) detected by flow cytometry (FIG. 11C). Then we injected the LS-542-labeled EPCs intravenously into mice with subcutaneous breast cancer, and found that they accumulated in the tumor specifically, which can be detected using an NIR imaging camera (FIG. 11D). These results demonstrated that the EPCs labeled can be loaded with imaging agents (such as the NIR dye LS-542), without changing their survival or migration to tumors, and be used for specific imaging.

The feasibility of using EPCs as a universal marker for imaging of different cancer types independent of their phenotype was further tested. First, we showed that the migration of EPCs was universal to all MM cell lines in vitro regardless of their surface biomarkers expression. Further, EPCs were labeled with near-infrared (NIR) tracer LS-542 and tested the staining intensity of the tracer in the EPCs, as well as its effect on viability and functionality of the EPCs. It was found that the EPCs demonstrated profound uptake of the tracer and became 3-fold of magnitude more fluorescent than non-labeled cells. At the same time, the labeling with LS-542 did not induce any cell toxicity in the EPC's, and it did not affect its migration properties to MM media in vitro. Therefore it is suggested that EPCs loaded with NIR dyes could be a universal strategy for imaging MM as well as other cancer.

(viii) EPCs Loaded with a Variety of Imaging Agents for PET and MRI Imaging.

To demonstrate that EPCs can be loaded with clinically-used imaging modalities such as PET and MRI, EPCs were efficiently radiolabeled with $^{18}$F-FDG (FIG. 12A) and $^{89}$Zr-oxine (FIG. 12B) used for PET imaging of tumors, the loading of EPCs with the PET-imaging agents was confirmed using gamma counter. Moreover, EPCs were loaded with $^{64}$Gd which is known as a contrast agent used for improved MRI imaging, the loading of Gd to the EPCs was confirmed using ICP-MS (FIG. 12C). These results demonstrated that the EPCs can be loaded with a variety of imaging agents and can be utilized for different imaging modalities such as PET and MRI.

(ix) EPCs Loaded with a Variety of Imaging Agents for PET and MRI Imaging.

To demonstrate that EPCs can be loaded with clinically-used imaging modalities such as PET and MRI, EPCs were efficiently radiolabeled with $^{18}$F-FDG (FIG. 12A) and $^{89}$Zr-oxine (FIG. 12B) used for PET imaging of tumors, the loading of EPCs with the PET-imaging agents was confirmed using gamma counter. Moreover, EPCs were loaded with $^{64}$Gd which is known as a contrast agent used for improved MRI imaging, the loading of Gd to the EPCs was confirmed using ICP-MS (FIG. 12C). These results demonstrated that the EPCs can be loaded with a variety of imaging agents and can be utilized for different imaging modalities such as PET and MRI.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A delivery system comprising a population of primed endothelial progenitor cells (EPCs) labeled with a photo- or radiation-activated anti-cancer prodrug, wherein the population of EPCs is obtained by culturing EPCs with a priming medium, wherein the priming medium is a cancer cell condition medium, or a hypoxic cancer cell conditioned medium, wherein the anti-cancer prodrug is Bortezomib, Titanocene, or 4-Borono-L-Phenylalanine.

2. The delivery system of claim 1, wherein the population of primed EPCs is obtained from bone marrow, peripheral blood, cord blood, or fat tissue.

3. The delivery system of claim 1, wherein the population of primed EPCs are generated from a pluripotent stem cell or an induced pluripotent stem cell.

4. A delivery system comprising a population of primed endothelial progenitor cells (EPCs) labeled with a photo- or radiation-activated anti-cancer prodrug, wherein the population of EPCs is obtained by culturing EPCs with a priming medium, wherein the priming medium is a hypoxic cancer cell conditioned medium.

5. The delivery system of claim 4, wherein the population of primed EPCs is obtained from bone marrow, peripheral blood, cord blood, or fat tissue.

6. The delivery system of claim 4, wherein the population of primed EPCs are generated from a pluripotent stem cell or an induced pluripotent stem cell.

7. The delivery system of claim 4, wherein the anti-cancer prodrug is Bortezomib, Titanocene, or 4-Borono-L-Phenylalanine.

* * * * *